(12) United States Patent
Koishihara et al.

(10) Patent No.: US 10,704,109 B2
(45) Date of Patent: Jul. 7, 2020

(54) **MARKER ASSOCIATED WITH EVERBEARING PROPERTIES IN PLANT OF GENUS *FRAGARIA* AND USE THEREOF**

(71) Applicant: TOYOTA JIDOSHA KABUSHIKI KAISHA, Toyota-shi, Aichi (JP)

(72) Inventors: Hiroaki Koishihara, Nagoya (JP); Hiroyuki Enoki, Hamamatsu (JP); Masayoshi Muramatsu, Miyoshi (JP); Satoru Nishimura, Nagoya (JP); Susumu Yui, Morioka (JP); Masanori Honjo, Morioka (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 74 days.

(21) Appl. No.: 15/558,597

(22) PCT Filed: Mar. 18, 2016

(86) PCT No.: PCT/JP2016/058693
§ 371 (c)(1),
(2) Date: Sep. 15, 2017

(87) PCT Pub. No.: WO2016/148275
PCT Pub. Date: Sep. 22, 2016

(65) Prior Publication Data
US 2018/0080036 A1    Mar. 22, 2018

(30) Foreign Application Priority Data

Mar. 18, 2015 (JP) .................................. 2015-054707
Mar. 4, 2016 (JP) .................................. 2016-042009

(51) Int. Cl.
*C12Q 1/68* (2018.01)
*C12Q 1/6895* (2018.01)

(52) U.S. Cl.
CPC .................................. *C12Q 1/6895* (2013.01)

(58) Field of Classification Search
None
See application file for complete search history.

(56) References Cited

U.S. PATENT DOCUMENTS

2016/0201145 A1    7/2016    Enoki et al.

FOREIGN PATENT DOCUMENTS

JP    2006-042622 A    2/2006
WO    2015/034040 A1    3/2015

OTHER PUBLICATIONS

Weebadde et al. (Plant Breeding 127, 94-101 (2008)) (Year: 2008).*
Hirakawa et al. (DNA Research, vol. 21, pp. 169-181, Nov. 2013) (Year: 2013).*
Strawberry Garden Blast search results. May 20, 2019. six pages. Obtained from strawberry-garden.kazusa.or.jp/cgi-bin/blast.cgi#FAN_iscf00157969.1 on May 20, 2019 (Year: 2019).*
"Seasonal strawberry suitable for cake "Miyazaki-natsuharuka"", Miyazaki Prefectural Agricultural Experimental Laboratory, Nov. 2, 2007 (2 pages total).
Yoshihisa Yamamoto et al., "Selection of DNA Markers for the Everbearing Gene of Strawberry," Kinki Chugoku Shikoku Agricultural Research, Mar. 31, 2003, pp. 42-44, No. 2.
Naoki Chiba, "Shiki Narisei Ichigo no DNA Marker o Katsuyo shita Senbatsu no Genjo to Mondaiten," Horticultural Research (Japan) separate volume, Sep. 27, 2008, pp. 60-61, vol. 7, No. 2.
Masanori Honjo et al., "The applicability of SSR markers for the discrimination of everbearing individuals among different lineages of everbearing strawberry," Horticultural Research (Japan) separate volume, Mar. 23, 2013, p. 326, vol. 12, No. 1.
T. Sugimoto et al., "Detection of RAPD markers linked to the everbearing gene in Japanese cultivated strawberry," Plant Breeding, 2005, pp. 498-501, vol. 124.
M. Honjo et al., "Detection of SSR markers linked to the everbearing gene in cultivated strawberry," Breeding Research, 2011, p. 265, vol. 13 (additional vol. 2).

* cited by examiner

*Primary Examiner* — Juliet C Switzer
(74) *Attorney, Agent, or Firm* — Sughrue Mion, PLLC

(57) ABSTRACT

This invention intends to develop many DNA markers for a plant of the genus *Fragaria* and identify everbearing lines with high precision by using the many DNA markers. The marker associated with everbearing properties in a plant of the genus *Fragaria* comprises a continuous nucleic acid region sandwiched between the nucleotide sequence as shown in SEQ ID NO: 1 and the nucleotide sequence as shown in SEQ ID NO: 5 in the chromosome of the plant of the genus *Fragaria*.

4 Claims, 21 Drawing Sheets
Specification includes a Sequence Listing.

Fig. 5-1

Phenotypes concerning everbearing property/one-season bearing property of hybrid progenies (F1) in Populations A and B

| Miyazaki Natsu Haruka x 08 To-f | | Miyazaki Natsu Haruka x Ohkimi | |
|---|---|---|---|
| Lineage | Seasonality | Lineage | Seasonality |
| A01 | 1 | B01 | 1 |
| A02 | 0 | B02 | 1 |
| A03 | 0 | B03 | 1 |
| A04 | 0 | B04 | 0 |
| A05 | 1 | B05 | 0 |
| A06 | 1 | B06 | 1 |
| A07 | 1 | B07 | 0 |
| A08 | 0 | B08 | 0 |
| A09 | 0 | B09 | 0 |
| A10 | 0 | B10 | 1 |
| A11 | 0 | B11 | 1 |
| A12 | 1 | B12 | 0 |
| A13 | 1 | B13 | 1 |
| A14 | 1 | B14 | 0 |
| A15 | 0 | B15 | 0 |
| A16 | 1 | B16 | 1 |
| A17 | 1 | B17 | 1 |
| A18 | 0 | B18 | 0 |
| A19 | 1 | B19 | 1 |
| A20 | 0 | B20 | 0 |
| A21 | 0 | B21 | 0 |
| A22 | 1 | B22 | 0 |
| A23 | 0 | B23 | 0 |
| A24 | 1 | B24 | 1 |
| A25 | 0 | B25 | 1 |
| A26 | 1 | B26 | 1 |
| A27 | 0 | B27 | 0 |
| A29 | 0 | B28 | 1 |
| A30 | 0 | B29 | 1 |
| A31 | 1 | B30 | 1 |
| A32 | 1 | B31 | 0 |
| A33 | 1 | B32 | 0 |
| A34 | 1 | B33 | 0 |
| A35 | 1 | B34 | 1 |

Fig. 5-2

| Miyazaki Natsu Haruka x 08 To-f | | Miyazaki Natsu Haruka x Ohkimi | |
|---|---|---|---|
| Lineage | Seasonality | Lineage | Seasonality |
| A36 | 0 | B35 | 1 |
| A37 | 1 | B36 | 0 |
| A38 | 0 | B37 | 1 |
| A39 | 1 | B38 | 1 |
| A40 | 0 | B39 | 0 |
| A41 | 0 | B40 | 0 |
| A42 | 0 | B41 | 0 |
| A43 | 0 | B42 | 1 |
| A44 | 1 | | |
| A45 | 0 | | |
| A46 | 0 | | |
| A47 | 1 | | |
| A48 | 0 | | |
| A49 | 0 | | |
| A50 | 0 | | |
| A51 | 1 | | |

* 1: Everbearing; 0: One-season-bearing

Fig. 6-1

Markers of 20th linkage group of Miyazaki Natsu Haruka in Miyazaki Natsu Haruka, 08 To-f, and novel hybrid progeny (F1, Population A)

| Linkage group | Marker name | Miyazaki Natsu Haruka | 08 To-f | F1 1 | 2 | 3 | 4 | 5 | 6 | 7 | 8 | 9 | 10 |
|---|---|---|---|---|---|---|---|---|---|---|---|---|---|
| 20th linkage group of Miyazaki Natsu Haruka | IB204594R | 49137 | 13841 | 13936 | 52227 | 49994 | 51693 | 14985 | 14295 | 16052 | 51632 | 47122 | 50307 |
| | IBA38559 | 7851 | 287 | 3292 | 283 | 274 | 306 | 5084 | 8873 | 10905 | 238 | 372 | 273 |
| | IB306953 | 59147 | 18349 | 55292 | 16228 | 15320 | 15446 | 50671 | 56334 | 51625 | 13862 | 16780 | 18482 |
| | IB303507R | 14573 | 464 | 308 | 13083 | 14146 | 14403 | 250 | 343 | 356 | 16234 | 14419 | 14412 |
| | IB303642R | 38268 | 17970 | 17948 | 41289 | 41019 | 14543 | 17721 | 17075 | 16424 | 38393 | 39415 | 41403 |
| Seasonality | | Everbearing | One-season-bearing | Everbearing | One-season-bearing | One-season-bearing | One-season-bearing | Everbearing | Everbearing | Everbearing | One-season-bearing | One-season-bearing | One-season-bearing |

| Linkage group | Marker name | F1 11 | 12 | 13 | 14 | 15 | 16 | 17 | 18 | 19 | 20 |
|---|---|---|---|---|---|---|---|---|---|---|---|
| 20th linkage group of Miyazaki Natsu Haruka | IB204594R | 51319 | 10880 | 16429 | 17321 | 53170 | 17428 | 15461 | 47797 | 13126 | 45033 |
| | IBA38559 | 269 | 9804 | 4700 | 6619 | 291 | 12459 | 8457 | 253 | 5658 | 237 |
| | IB306953 | 16892 | 61430 | 52582 | 54348 | 16702 | 51791 | 15583 | 16522 | 57452 | 19458 |
| | IB303507R | 14328 | 244 | 279 | 251 | 12796 | 328 | 16966 | 16878 | 282 | 10952 |
| | IB303642R | 40228 | 14434 | 14016 | 16195 | 38275 | 15718 | 10174 | 37973 | 15451 | 41152 |
| Seasonality | | One-season-bearing | Everbearing | Everbearing | Everbearing | One-season-bearing | Everbearing | Everbearing | One-season-bearing | Everbearing | One-season-bearing |

Fig. 6-2

| Linkage group | Marker name | F1 | | | | | | | | | |
|---|---|---|---|---|---|---|---|---|---|---|---|
| | | 21 | 22 | 23 | 24 | 25 | 26 | 27 | 29 | 30 | |
| 20th linkage group of Miyazaki | IB204594R | 46111 | 17337 | 49343 | 12645 | 51592 | 17175 | 55354 | 51483 | 50891 | |
| | IBA38559 | 266 | 258 | 245 | 3723 | 268 | 11737 | 300 | 262 | 234 | |
| | IB306953 | 14645 | 16671 | 15439 | 50914 | 51800 | 54790 | 14591 | 14230 | 15208 | |
| Natsu | IB303507R | 15710 | 14989 | 16652 | 231 | 249 | 370 | 14837 | 13338 | 14457 | |
| Haruka | IB303642R | 34747 | 15086 | 41537 | 12989 | 40090 | 15282 | 42448 | 38005 | 44562 | |
| Seasonality | | One-season-bearing | Everbearing | One-season-bearing | Everbearing | One-season-bearing | Everbearing | One-season-bearing | One-season-bearing | One-season-bearing | |

| Linkage group | Marker name | F1 | | | | | | | | | |
|---|---|---|---|---|---|---|---|---|---|---|---|
| | | 31 | 32 | 33 | 34 | 35 | 36 | 37 | 38 | 39 | 40 |
| 20th linkage group of Miyazaki | IB204594R | 14386 | 13238 | 16413 | 16248 | 15384 | 52588 | 16675 | 51584 | 16200 | 51095 |
| | IBA38559 | 13305 | 9470 | 7656 | 4591 | 7429 | 246 | 7016 | 269 | 8753 | 313 |
| | IB306953 | 55641 | 55571 | 59939 | 56982 | 53111 | 14884 | 57987 | 17862 | 54359 | 16992 |
| Natsu | IB303507R | 302 | 390 | 256 | 262 | 267 | 15527 | 250 | 13647 | 314 | 14700 |
| Haruka | IB303642R | 16355 | 16515 | 16320 | 15430 | 17333 | 43598 | 16001 | 41436 | 18140 | 43049 |
| Seasonality | | Everbearing | Everbearing | Everbearing | Everbearing | Everbearing | One-season-bearing | Everbearing | One-season-bearing | Everbearing | One-season-bearing |

Fig. 6-3

| Linkage group | Marker name | F1 | | | | | | | | | | | Concordance with phenotype |
|---|---|---|---|---|---|---|---|---|---|---|---|---|---|
| | | 41 | 42 | 43 | 44 | 45 | 46 | 47 | 48 | 49 | 50 | 51 | |
| 20th linkage group of Miyazaki Natsu Haruka | IB204594R | 47950 | 12204 | 53769 | 16982 | 51824 | 51845 | 13999 | 50631 | 45513 | 49657 | 17451 | 98% |
| | IBA38559 | 267 | 12845 | 251 | 8917 | 250 | 328 | 6712 | 302 | 234 | 265 | 5585 | 96% |
| | IB306953 | 16187 | 55588 | 16622 | 57344 | 17614 | 13938 | 58664 | 16488 | 14702 | 16009 | 52715 | 92% |
| | IB303507R | 15216 | 299 | 14431 | 261 | 14825 | 13605 | 249 | 15579 | 14217 | 14018 | 283 | 92% |
| | IB303642R | 40538 | 17188 | 41812 | 16690 | 42002 | 39075 | 18179 | 40655 | 41784 | 42679 | 17809 | 98% |
| Seasonality | | One-season-bearing | One-season-bearing | One-season-bearing | Everbearing | One-season-bearing | One-season-bearing | Everbearing | One-season-bearing | One-season-bearing | One-season-bearing | Everbearing | |

Fig. 9-1

Phenotypes concerning everbearing property/one-season-bearing property of hybrid progenies (F1) in Populations A and B and results of PCR and electrophoresis of IB204594R marker of 20th linkage group of Miyazaki Natsu Haruka

| Miyazaki Natsu Haruka × 08 To-f ||| Miyazaki Natsu Haruka × Ohkimi |||
| --- | --- | --- | --- | --- | --- |
| Lineage | Seasonality | Results attained using PCR base marker | Lineage | Seasonality | Results attained using PCR base marker |
| A01 | 1 | 1 | B01 | 1 | 1 |
| A02 | 0 | 0 | B02 | 1 | 1 |
| A03 | 0 | 0 | B03 | 1 | 1 |
| A04 | 0 | 0 | B04 | 0 | 0 |
| A05 | 1 | 1 | B05 | 0 | 0 |
| A06 | 1 | 1 | B06 | 1 | 1 |
| A07 | 1 | 1 | B07 | 0 | 0 |
| A08 | 0 | 0 | B08 | 0 | 0 |
| A09 | 0 | 0 | B09 | 0 | 0 |
| A10 | 0 | 0 | B10 | 1 | 1 |
| A11 | 0 | 0 | B11 | 1 | 1 |
| A12 | 1 | 1 | B12 | 0 | 0 |
| A13 | 1 | 1 | B13 | 1 | 1 |
| A14 | 1 | 1 | B14 | 0 | 0 |
| A15 | 0 | 0 | B15 | 0 | 1 |
| A16 | 1 | 1 | B16 | 1 | 1 |
| A17 | 1 | 1 | B17 | 1 | 1 |
| A18 | 0 | 0 | B18 | 0 | 0 |
| A19 | 1 | 1 | B19 | 1 | 1 |
| A20 | 0 | 0 | B20 | 0 | 0 |
| A21 | 0 | 0 | B21 | 0 | 0 |
| A22 | 1 | 1 | B22 | 0 | 0 |
| A23 | 0 | 0 | B23 | 0 | 0 |
| A24 | 1 | 1 | B24 | 1 | 1 |
| A25 | 0 | 0 | B25 | 1 | 1 |
| A26 | 1 | 1 | B26 | 1 | 1 |
| A27 | 0 | 0 | B27 | 0 | 0 |
| A29 | 0 | 0 | B28 | 1 | 1 |
| A30 | 0 | 0 | B29 | 1 | 1 |
| A31 | 1 | 1 | B30 | 1 | 1 |
| A32 | 1 | 1 | B31 | 0 | 0 |

Fig. 9-2

| Miyazaki Natsu Haruka × 08 To-f | | | Miyazaki Natsu Haruka × Ohkimi | | |
|---|---|---|---|---|---|
| Lineage | Seasonality | Results attained using PCR base marker | Lineage | Seasonality | Results attained using PCR base marker |
| A33 | 1 | 1 | B32 | 0 | 0 |
| A34 | 1 | 1 | B33 | 0 | 0 |
| A35 | 1 | 1 | B34 | 1 | 1 |
| A36 | 0 | 0 | B35 | 1 | 1 |
| A37 | 1 | 1 | B36 | 0 | 0 |
| A38 | 0 | 0 | B37 | 1 | 1 |
| A39 | 1 | 1 | B38 | 1 | 1 |
| A40 | 0 | 0 | B39 | 0 | 1 |
| A41 | 0 | 0 | B40 | 0 | 0 |
| A42 | 0 | 1 | B41 | 0 | 0 |
| A43 | 0 | 0 | B42 | 1 | 1 |
| A44 | 1 | 1 | | | |
| A45 | 0 | 0 | | | |
| A46 | 0 | 0 | | | |
| A47 | 1 | 1 | | | |
| A48 | 0 | 0 | | | |
| A49 | 0 | 0 | | | |
| A50 | 0 | 0 | | | |
| A51 | 1 | 1 | | | |

\* 1: Everbearing; 0: one-season-bearing
\* PCR base marker: 0: band detected; 1: no band detected

Fig. 12-1

Phenotypes concerning everbearing property/one-season-bearing property of hybrid progenies (F1) in Populations A and B and results of PCR and electrophoresis of IB38559 marker of 20th linkage group of Miyazaki Natsu Haruka

| Miyazaki Natsu Haruka × 08 To-f ||| Miyazaki Natsu Haruka × Ohkimi |||
|---|---|---|---|---|---|
| Lineage | Seasonality | Results attained using PCR base marker | Lineage | Seasonality | Results attained using PCR base marker |
| A01 | 1 | 1 | B01 | 1 | 1 |
| A02 | 0 | 0 | B02 | 1 | 1 |
| A03 | 0 | 0 | B03 | 1 | 1 |
| A04 | 0 | 0 | B04 | 0 | 0 |
| A05 | 1 | 1 | B05 | 0 | 0 |
| A06 | 1 | 1 | B06 | 1 | 1 |
| A07 | 1 | 1 | B07 | 0 | 0 |
| A08 | 0 | 0 | B08 | 0 | 0 |
| A09 | 0 | 0 | B09 | 0 | 0 |
| A10 | 0 | 0 | B10 | 1 | 1 |
| A11 | 0 | 0 | B11 | 1 | 1 |
| A12 | 1 | 1 | B12 | 0 | 0 |
| A13 | 1 | 1 | B13 | 1 | 1 |
| A14 | 1 | 1 | B14 | 0 | 0 |
| A15 | 0 | 0 | B15 | 0 | 1 |
| A16 | 1 | 1 | B16 | 1 | 1 |
| A17 | 1 | 1 | B17 | 1 | 1 |
| A18 | 0 | 0 | B18 | 0 | 0 |
| A19 | 1 | 1 | B19 | 1 | 1 |
| A20 | 0 | 0 | B20 | 0 | 0 |
| A21 | 0 | 0 | B21 | 0 | 0 |
| A22 | 1 | 0 | B22 | 0 | 0 |
| A23 | 0 | 0 | B23 | 0 | 0 |
| A24 | 1 | 1 | B24 | 1 | 1 |
| A25 | 0 | 0 | B25 | 1 | 1 |
| A26 | 1 | 1 | B26 | 1 | 1 |
| A27 | 0 | 0 | B27 | 0 | 0 |
| A29 | 0 | 0 | B28 | 1 | 1 |
| A30 | 0 | 0 | B29 | 1 | 1 |
| A31 | 1 | 1 | B30 | 1 | 1 |
| A32 | 1 | 1 | B31 | 0 | 0 |

Fig. 12-2

| Miyazaki Natsu Haruka × 08 To-f | | | Miyazaki Natsu Haruka × Ohkimi | | |
|---|---|---|---|---|---|
| Lineage | Seasonality | Results attained using PCR base marker | Lineage | Seasonality | Results attained using PCR base marker |
| A33 | 1 | 1 | B32 | 0 | 0 |
| A34 | 1 | 1 | B33 | 0 | 0 |
| A35 | 1 | 1 | B34 | 1 | 1 |
| A36 | 0 | 0 | B35 | 1 | 1 |
| A37 | 1 | 1 | B36 | 0 | 0 |
| A38 | 0 | 0 | B37 | 1 | 1 |
| A39 | 1 | 1 | B38 | 1 | 1 |
| A40 | 0 | 0 | B39 | <u>0</u> | <u>1</u> |
| A41 | 0 | 0 | B40 | 0 | 0 |
| A42 | <u>0</u> | <u>1</u> | B41 | 0 | 0 |
| A43 | 0 | 0 | B42 | 1 | 1 |
| A44 | 1 | 1 | | | |
| A45 | 0 | 0 | | | |
| A46 | 0 | 0 | | | |
| A47 | 1 | 1 | | | |
| A48 | 0 | 0 | | | |
| A49 | 0 | 0 | | | |
| A50 | 0 | 0 | | | |
| A51 | 1 | 1 | | | |

* 1: Everbearing; 0: one-season-bearing
* PCR base marker: 0: band detected; 1: no band detected

MARKER ASSOCIATED WITH EVERBEARING PROPERTIES IN PLANT OF GENUS *FRAGARIA* AND USE THEREOF

CROSS REFERENCE TO RELATED APPLICATIONS

This application is a National Stage of International Application No. PCT/JP2016/058693 filed Mar. 18, 2016, claiming priority based on Japanese Patent Application No. 2015-054707 filed Mar. 18, 2015 and Japanese Patent Application No. 2016-042009 filed Mar. 4, 2016, the contents of all of which are incorporated herein by reference in their entirety.

TECHNICAL FIELD

The present invention relates to a marker associated with everbearing properties that enables selection of an everbearing plant line of the genus *Fragaria* and use thereof.

BACKGROUND ART

With the development of DNA markers (also referred to as genetic markers or gene markers), both useful and undesirable traits can be rapidly and efficiently identified when improvement in plant varieties is intended. The development of DNA markers has advanced for a wide variety of practical plants as well as for model plants such as *Arabidopsis thaliana* and *Oryza sativa*. Thus, such markers significantly contribute to improvement in plant varieties.

Strawberries are known to be classified into one-season-bearing varieties and everbearing varieties. One-season-bearing varieties undergo floral bud formation under low-temperature and short-day conditions in autumn and flowering and fruiting in the following spring. Everbearing varieties naturally undergo floral bud differentiation under long-day and high-temperature conditions and thus undergo fruiting from summer to autumn in addition to spring. An example of a known variety of the latter is "Summerberry." Since everbearing varieties are able to match demands in seasons when one-season-bearing varieties cannot be harvested, the development of improved everbearing varieties has been desired.

Sugimoto et al., 2005, Plant Breeding 124: 498-501 and Yamamoto et al., 2003. Kinki Chugoku Shikoku Agricultural Research 2: 42-44 describe that the F1 progeny generation resulting from the cross between an everbearing variety "Everberry" and a one-season-bearing variety "Toyonoka" was used to identify the RAPD marker associated with a gene associated with everbearing properties. However, the RAPD marker disclosed in Sugimoto et al., 2005, Plant Breeding 124: 498-501 and Yamamoto et al., 2003, Kinki Chugoku Shikoku Agricultural Research 2: 42-44 has drawbacks, such that the degree of linkage thereof to the gene associated with everbearing properties is low, the selection efficiency is poor, and it is thus not suitable for practical use.

JP 2006-42622 A discloses a DNA marker located in the vicinity of the gene associated with everbearing properties in strawberries, a primer used for amplifying such marker, and a method for distinguishing everbearing varieties from one-season-bearing varieties with the use of such marker in a simple manner. The DNA marker disclosed in JP 2006-42622 A is an ISSR marker, which is problematic in terms of convenience and accuracy in distinguishing. When the DNA marker disclosed in JP 2006-42622 A is amplified, for example, a plurality of bands appear from a single analyte. However, the target band is located in a position very close to other bands, and it is difficult to distinguish the target band from other bands. In addition, the degree of linkage thereof to phenotypes exhibiting everbearing properties is not strong, and the accuracy in selection is thus low.

In addition, Honjo et al., 2011, Breeding Research 13 (Additional Vol. 2): 265 discloses an SSR marker that is strongly linked to everbearing properties. The SSR marker disclosed in Honjo et al., 2011, Breeding Research 13 (Additional Vol. 2): 265 requires the use of an expensive electrophoresis apparatus with high accuracy for analysis, which could not be used conveniently for a simple test.

SUMMARY OF THE INVENTION

Objects to be Attained by the Invention

To date, the DNA marker technologies concerning everbearing properties in plant lines of the genus *Fragaria* as described above could not be regarded as sufficient in terms of the logarithm of odds (LOD) and the contribution ratio, and such markers could not be evaluated as excellent markers.

Under the above circumstances, it is an object of the present invention to develop many DNA markers in plants of the genus *Fragaria*, which are polyploids with complex genomic structures, and to provide markers associated with everbearing properties that enable evaluation of everbearing properties with high accuracy with the use of such many DNA markers and to provide a method of using such markers.

Means for Attaining the Objects

The present inventors have conducted concentrated studies in order to attain the above objects. As a result, they discovered markers linked to everbearing properties by preparing many markers in plants of the genus *Fragaria* and conducting linkage analysis between quantitative traits and markers in hybrid progeny lines. This has led to the completion of the present invention.

The present invention includes the following.

(1) A marker associated with everbearing properties in plants of the genus *Fragaria* comprising a continuous nucleic acid region sandwiched between the nucleotide sequence as shown in SEQ ID NO: 1 and the nucleotide sequence as shown in SEQ ID NO: 5 in the chromosome of the plant of the genus *Fragaria*.

(2) The marker associated with everbearing properties in plants of the genus *Fragaria* according to (1), wherein the nucleic acid region comprises any nucleotide sequence selected from the group consisting of nucleotide sequences as shown in SEQ ID NOs: 1 to 5 or a part of the nucleotide sequence.

(3) The marker associated with everbearing properties in plants of the genus *Fragaria* according to (1), wherein the nucleic acid region is located in a region sandwiched between the nucleotide sequence as shown in SEQ ID NO: 3 and the nucleotide sequence as shown in SEQ ID NO: 4 in the chromosome of the plant of the genus *Fragaria*.

(4) A method for producing a plant line of the genus *Fragaria* with everbearing properties comprising:

a step of extracting a chromosome of a progeny plant whose at least one parent is a plant of the genus *Fragaria* and/or a chromosome of the parent plant of the genus *Fragaria*; and a step of determining the presence or absence of the marker associated with everbearing properties in the plant of the genus *Fragaria* according to any one of (1) to (3) in the chromosome obtained above.

(5) The method for producing a plant line of the genus *Fragaria* according to (4), wherein the step of determination comprises conducting a nucleic acid amplification reaction using a primer that specifically amplifies the marker associated with everbearing properties in the plant of the genus *Fragaria* to determine the presence or absence of the marker associated with everbearing properties in the plant of the genus *Fragaria*.

(6) The method for producing a plant line of the genus *Fragaria* according to (4), wherein the step of determination involves the use of a DNA chip comprising a probe corresponding to the marker associated with everbearing properties in the plant of the genus *Fragaria*.

(7) The method for producing a plant line of the genus *Fragaria* according to (4), wherein the progeny plant is a seed or seedling and the chromosome is extracted from the seed or seedling.

This description includes part or all of the content as disclosed in the descriptions and/or drawings of Japanese Patent Application Nos. 2015-054707 and 2016-042009, which are priority documents of the present application.

Effects of the Invention

The present invention provides novel markers associated with everbearing properties in plants of the genus *Fragaria* that are linked to everbearing properties among various traits of plants of the genus *Fragaria*. With the use of the markers associated with everbearing properties in plants of the genus *Fragaria* according to the present invention, everbearing properties in hybrid lines of the plants of the genus *Fragaria* can be tested. Thus, plant lines of the genus *Fragaria* exhibiting everbearing properties can be identified in a very cost-effective manner.

BRIEF DESCRIPTION OF THE DRAWINGS

FIG. 5-1 shows a characteristic diagram showing the results of inspection concerning everbearing properties in hybrid progeny lines of "Miyazaki Natsu Haruka" and "08 To-f" (Population A) and hybrid progeny lines of "Miyazaki Natsu Haruka" and "Ohkimi" (Population B).

FIG. 5-2 shows a characteristic diagram showing the results of inspection concerning everbearing properties in hybrid progeny lines of "Miyazaki Natsu Haruka" and "08 To-f" (Population A) and hybrid progeny lines of "Miyazaki Natsu Haruka" and "Ohkimi" (Population B).

FIG. 6-1 shows a characteristic diagram showing the results of comparison of the array signal values of the markers associated with everbearing properties in strawberries and the phenotypes of hybrid progeny lines of "Miyazaki Natsu Haruka" and "08 To-f" (Population A).

FIG. 6-2 shows a characteristic diagram showing the results of comparison of the array signal values of the markers associated with everbearing properties in strawberries and the phenotypes of hybrid progeny lines of "Miyazaki Natsu Haruka" and "08 To-f" (Population A).

FIG. 6-3 shows a characteristic diagram showing the results of comparison of the array signal values of the markers associated with everbearing properties in strawberries and the phenotypes of hybrid progeny lines of "Miyazaki Natsu Haruka" and "08 To-f" (Population A).

FIG. 7-1 shows electrophoresis images showing the results of PCR carried out with the use of a primer that specifically amplifies the marker IB204594R of hybrid progeny lines of "Miyazaki Natsu Haruka" and "08 To-f" (Population A).

FIG. 7-2 shows electrophoresis images showing the results of PCR carried out with the use of a primer that specifically amplifies the marker IB204594R of hybrid progeny lines of "Miyazaki Natsu Haruka" and "08 To-f" (Population A).

FIG. 8-1 shows electrophoresis images showing the results of PCR carried out with the use of a primer that specifically amplifies the marker IB204594R of hybrid progeny lines of "Miyazaki Natsu Haruka" and "Ohkimi" (Population B).

FIG. 8-2 shows electrophoresis images showing the results of PCR carried out with the use of a primer that specifically amplifies the marker IB204594R of hybrid progeny lines of "Miyazaki Natsu Haruka" and "Ohkimi" (Population B).

FIG. 9-1 shows a characteristic diagram summarizing the results of PCR carried out with the use of a primer that specifically amplifies the marker IB204594R of hybrid progeny lines of "Miyazaki Natsu Haruka" and "08 To-f" (Population A) and hybrid progeny lines of "Miyazaki Natsu Haruka" and "Ohkimi" (Population B).

FIG. 9-2 shows a characteristic diagram summarizing the results of PCR carried out with the use of a primer that specifically amplifies the marker IB204594R of hybrid progeny lines of "Miyazaki Natsu Haruka" and "08 To-f" (Population A) and hybrid progeny lines of "Miyazaki Natsu Haruka" and "Ohkimi" (Population B).

FIG. 10-1 shows electrophoresis images showing the results of PCR carried out with the use of a primer that specifically amplifies the marker IBA38559 of hybrid progeny lines of "Miyazaki Natsu Haruka" and "08 To-f" (Population A).

FIG. 10-2 shows electrophoresis images showing the results of PCR carried out with the use of a primer that specifically amplifies the marker IBA38559 of hybrid progeny lines of "Miyazaki Natsu Haruka" and "08 To-f" (Population A).

FIG. 11-1 shows electrophoresis images showing the results of PCR carried out with the use of a primer that specifically amplifies the marker IBA38559 of hybrid progeny lines of "Miyazaki Natsu Haruka" and "Ohkimi" (Population B).

FIG. 11-2 shows electrophoresis images showing the results of PCR carried out with the use of a primer that specifically amplifies the marker IBA38559 of hybrid progeny lines of "Miyazaki Natsu Haruka" and "Ohkimi" (Population B).

FIG. 12-1 shows a characteristic diagram summarizing the results of PCR carried out with the use of a primer that specifically amplifies the marker IBA38559 of hybrid progeny lines of "Miyazaki Natsu Haruka" and "08 To-f" (Population A) and hybrid progeny lines of "Miyazaki Natsu Haruka" and "Ohkimi" (Population B).

FIG. 12-2 shows a characteristic diagram summarizing the results of PCR carried out with the use of a primer that specifically amplifies the marker IBA38559 of hybrid progeny lines of "Miyazaki Natsu Haruka" and "08 To-f" (Population A) and hybrid progeny lines of "Miyazaki Natsu Haruka" and "Ohkimi" (Population B).

EMBODIMENTS FOR CARRYING OUT THE INVENTION

Figure 1:
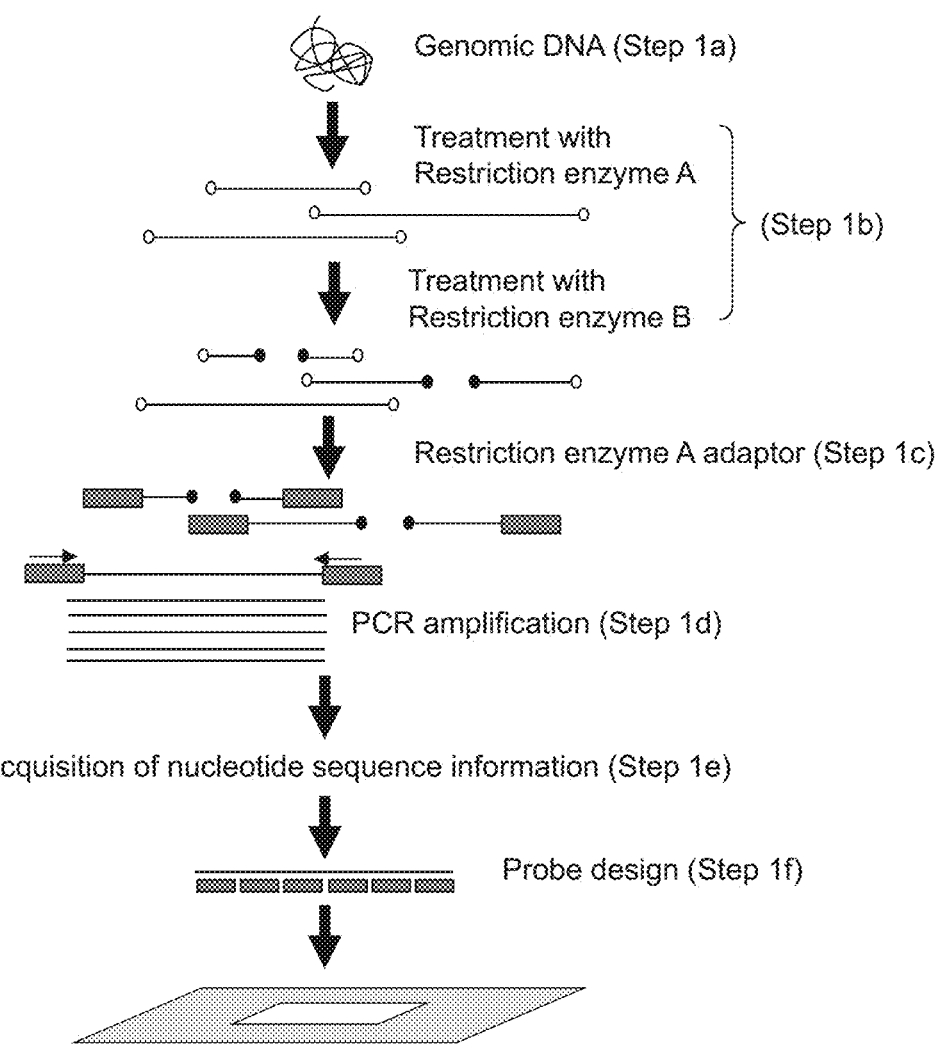
FIG. 1 schematically shows a process for producing a DNA microarray used for obtaining markers in chromosomes of plants of the genus *Fragaria*.

Hereafter, the markers associated with everbearing properties in plants of the genus *Fragaria* of the present invention, the method for using the same, and, in particular, a method for producing plant lines of the genus *Fragaria* using the markers associated with everbearing properties in plants of the genus *Fragaria* are described.

[Markers Associated with Everbearing Properties in Plants of the Genus *Fragaria*]

The marker associated with everbearing properties in plants of the genus *Fragaria* according to the present invention is a particular region in the chromosome of a plant of the genus *Fragaria* that makes it possible to identify traits of everbearing properties in a plant of the genus *Fragaria*. By determining the presence or absence of the marker associated with everbearing properties in the plant of the genus *Fragaria* in the progeny lines obtained from existing plants of the genus *Fragaria*, specifically, whether or not a line of interest has everbearing properties can be determined. In the present invention, the traits of "everbearing properties" refer to traits such that, in open-field culture in under natural conditions in Japan, a plant undergoes flowering in spring, floral bud differentiation again under high-temperature and long-day conditions from spring to early summer, and flowering is also observed from summer to autumn. Everbearing properties can be evaluated based on whether or not floral bunds are formed from summer to autumn under natural conditions as described above. In addition, plants may be cultured under artificial long-day conditions (a light period of 16 to 24 hours), and whether or not flowering would take place may then be inspected.

The term "a marker associated with everbearing properties in plants of the genus *Fragaria*" refers to a marker linked to traits exhibiting everbearing properties. When the marker associated with everbearing properties in plants of the genus *Fragaria* is present in a given plant of the genus *Fragaria*, for example, such plant can be determined to be of an everbearing variety. In particular, the marker associated with everbearing properties in plants of the genus *Fragaria* may be considered to be a region linked to a causal gene (or causal genes) of traits associated with everbearing properties in plants of the genus *Fragaria*.

The term "plants of the genus *Fragaria*" used herein refers to all plants belonging to the rosaceous genus *Fragaria* (*Fragaria* L.). Specific examples of plants of the genus *Fragaria* include hybrids of general strawberry cultivars, *Fragaria ananassa* (i.e., *Fragaria×ananassa*). Examples of plants of the genus *Fragaria* include plants of *F. virginiana* that are progenitor species of strawberry cultivars and plants of wild species, such as *F. chiloensis. F. vesca, F. iinumae. F. nipponica. F. nilgerrensis, F. nubicola. F. bucharica, F. daltoniana, F. orientalis, F. corimbosa. F. moschata*, and *F. iturupensis*. Further, "plants of the genus *Fragaria*" encompass known varieties and lines of strawberry cultivars (*F.×ananassa*).

Known varieties and lines of strawberry cultivars are not particularly limited, and any varieties and lines that can be used inside or outside Japan are within the scope thereof. For example, strawberry varieties grown in Japan are not particularly limited. Examples thereof include Toyonoka, Sanchigo, June berry, Nyohou, Pisutoro, Rindamore, Tochiotome, Aisutoro, Tochinomine, Akihime, Benihoppe, Tochihime, Sachinoka, Keikiwase, Sagahonoka, Aiberry, Karen berry. Red pearl, Satsumaotome, Fukuoka S6 (Amaou), Nohime, Hinomine, and Houkou-wase.

The presence or absence of the marker associated with everbearing properties in plants of the genus *Fragaria* can be determined in the above plants of the genus *Fragaria* and progeny lines of the above plants of the genus *Fragaria*. In a progeny line, either the mother plant or father plant may be a plant of the genus *Fragaria* described above. A progeny line may result from sibling crossing or may be a hybrid line. Alternatively, a progeny line may result from so-called back crossing.

It is particularly preferable that the presence or absence of the marker associated with everbearing properties in the plant of the genus *Fragaria* be determined in strawberry cultivars (*F.×ananassa*). In addition, it is preferable that the presence or absence of the marker associated with everbearing properties in the plant of the genus *Fragaria* be determined in improved lines resulting from various varieties and lines of the strawberry cultivars described above. In such a case, everbearing properties in strawberries can be evaluated in produced new varieties. Accordingly, it is preferable that a new variety be derived from a line having everbearing properties in strawberries as either the mother plant or father plant.

The marker associated with everbearing properties in plants of the genus *Fragaria* according to the present invention has been newly identified by QTL (Quantitative Trait Loci) analysis using a genetic linkage map containing 8,218 markers acquired from the strawberry variety "Miyazaki Natsu Haruka" and 8,039 markers acquired from the strawberry line "08 To-f" and data concerning everbearing properties in strawberries. QTL analysis is carried out with the use of the genetic analysis software of QTL Cartographer (Wang S., C. J. Basten and Z.-B. Zeng, 2010, Windows QTL Cartographer 2.5., Department of Statistics, North Carolina State University, Raleigh, N.C.) in accordance with the composite interval mapping (CIM) method.

Specifically, a region exhibiting a LOD score equivalent to or higher than a given threshold (e.g., 2.5) was found in the gene linkage maps by the QTL analysis. A size of a region is approximately 5.5 cM (centimorgan), and this region is included in the 20th linkage group of the strawberry line "Miyazaki Natsu Haruka." The unit "morgan (M)" relatively indicates a distance between genes on the chromosome, and such distance is represented in terms of a percentage of the crossing-over value. In the chromosome of a plant of the genus *Fragaria*, "1 cM" is equivalent to approximately 400 kb. This region has a peak whose LOD score is approximately 47.4. This implies the presence of a causal gene (or causal genes) that impart(s) everbearing properties to plants of the genus *Fragaria* at such peak or in the vicinity thereof.

The 5.5-cM region comprises the 5 types of markers shown in Table 1 in the order shown in Table 1. The marker names indicated in Table 1 were acquired exclusively for the present invention.

TABLE 1

| SEQ ID NO: | Marker name | Nucleotide sequence information |
|---|---|---|
| 1 | IB303507R | TTGATGTAGATATGATATATCAAAGAGAAGG AAAAGAAACTTTGCCACACTTAAGTCTACAA GCATATCTATACAAACACATTCGTTAAATGT CAATAGCATATCATCACAATTCAGTTGAAAT AGCATTCTAAACAGATGCTATTGTTCCTTCA GTAGATGCACCAAGGACTTCTGTGACTCTGT GTCCAGACTCCAAACTATCTCAAACCAGTAA GATAATTTCCTTTTTATACACTTCACACAAG AGAAAATGTTTAACCATCACTGATGCTAAGA CCAGATTGAAAGGTCCCGCTGCCAAACCATC TTGACCACATACAACAAAACATGACCTTTAG CACCATAAATTTTCCACAAGTACAAATTTAC AAGTTAAAACTGTTCAGTTAAACACCCCCAC CGTGACTTAATCACTCAAAGCAATTGAAAAG AAATCCAAGTTCCCAACTAGTAAACGTATTA CAATATTCCTCTCACAGCTTAAACGACAACC GATTATGTTGAGTTGCTAACCCTTTACATTG TTGCATTATGTGTTCTAAGAGCATTAATCTA AAACAATAAGGGGTCATTCACACCATTCTAA AGCGCACAATCAGAAGCTTTACTTTACTTCT CGAGCCAATTTCGCATATGTTACCCAAATCT TCACATAGTTCAAGCAAATCCAATTTTGCAA AACACCCAACAAAGCATGAATCGAATACTTA ACATTGCAACAATAAAAACAAAGTTTTCAAT |
| 2 | IB306953 | AATTCTGTAGAATCACCCAAAGATCTTAACG AGTTACCCCTTGAAGATGAAGAGTTCAGAAC GTGTGATGAAAAGTTTTCTGATGAAAAAGTA GCAGAGGAGGGAAGCAAAATGAAGAGGGGA CAGAAGTCGCAGATGCTTTCTCAAGGCAAGC AGATGAAGCTAGAAACACTGCTGTCTAAGTT TGTGGACAGGTAATTCCTACTCACGCACAGT TTAATTATTTAGTTCGTCATCCCTTCTCTCA TAAATACTCATATACTATGTTCTCTGAATTT TCAGGTCGAGTGCTGATGAAACATTGCTTCA CATGAATGATGATCCCTTTCTGAAGAATAGC TTAGTTTTTGTGTGATGGCCTGTGATTTTCT ATTGTGAAACTGTATCAGTAGTGTAAAAAAT TAAACATAAAATTGCTATCCTAAGAAGACT AGGATAGA |
| 3 | IBA38559 | CACATTGTTCTTCACTCCGCTTCCGAATAGC TATATCATTTTTCTGAGTGAACTTGGAACT AAAGCCTAGCTTGATTAATTCCATCTCGCCC GCCCATGTCTTGATTCCCTAAAACTAAACGA ATTGTTGTGGATTCCAAATGATTTGTATAAT ATTATGAATCGCCGTCAAAGTCTACCCGATT CAGAAACTCCAATAATTTACATGAACAAACA AAAGCCTGCGCAATAATTCATGCATGTTTCA TCTCAAACTCTCGAGGATTGATTCTCTCTGT CACATAAGAGCATATGCACTCCATACCCTCC A |
| 4 | IB204594R | TGTGCTTTCCAAGTTTCCATTTTTGTTTTAG ACTGATGAATTGTCCAAGTCCAAGCAATAAT ACCGCCAAAATCAACCGGTCATGATACTACT AATATGGAGCTTGTACTGTGGTCGACGACAG AAAGATCTTATCGACCCGATGATGAAACATC ATCTGTAACAGTTGAAGTGATATAACTTTGT AGTTGCTAGAACTTTGAAACGATAGGTCGTA ACGTATCAAAATTAAAACGTTAGACTAATAA ACCGGAGTACATGGTAACCTATGCTCTCGTT GCTATCATTAAGCCTCTCTCCCCACATAGGC AATCATATACCCTAGAGTCTTAGACTTTTTT TGGGTACGCAAACTGTCTCTTTTGCTGCGGG GCAGATGACCGAGGCAGAAAAATATATTAAC AGAGATACAAAATTTCTTGCGGTTAAATTT TAGTAACAATATATAAGCACGACTATAAG CATTACTTGCGGCTAATTTATGTGTACAAGA ATTGAAGTTTG |
| 5 | IB303642R | TTGGAATGCAGAACTTTTGTTGCTGTACTTA CGTAATTTTGTGTATAGTTGTTCACTTATCA TTTCTAGGCATCAAAGTTAGAATCTCCCTTA TCCAGAATTGGTATGGTTCTGTACAGTGTAA TTTAGCTATCTGTAATGAGCTTCATCCTTGA AGTTTCAATTCGGTAAGATCAAATATCCATC |

TABLE 1-continued

| SEQ ID NO: | Marker name | Nucleotide sequence information |
|---|---|---|
| | | CTTGTCTTGGAACAAAAGGCTAAGAAATGTT AATCATGTATTGACTATGGCACTACTAGTGA TTGCATATGTTAACTCAGAAATGTGATGTTT ACTTAGGTTGGGAGGTGGCCTATAAGCAACT ATTCTGATTCTTCACAATCAGTTTAGCAGTT GGAGTTTTATAAGCCAGCATATCCAATACAC CAATTGCAAGTCTCCACACAGCTCAAAATGA GTGTAGGAAACTAAAAATACTTCGGACTCCA TTCTGTGCATTAACAGTGAGAAACTGAGTAG GCGAGTAGAT |

Specifically, the marker associated with everbearing properties in plants of the genus *Fragaria* according to the present invention is a continuous nucleic acid region sandwiched between the nucleotide sequence as shown in SEQ ID NO: 1 and the nucleotide sequence as shown in SEQ ID NO: 5 in the chromosome of the plant of the genus *Fragaria*. The peak in the 5.5-cM region is located in a region sandwiched between the marker comprising the nucleotide sequence as shown in SEQ ID NO: 3 (IBA38559) and the marker comprising the nucleotide sequence as shown in SEQ ID NO: 4 (IB204594R).

The 5 types of markers shown in Table 1 include both of markers linked to traits that exhibit everbearing properties (i.e., coupling markers) and markers linked to traits that do not exhibit everbearing properties (i.e., reciprocal markers). The marker comprising the nucleotide sequence as shown in SEQ ID NO: 1 (IB303507R), the marker comprising the nucleotide sequence as shown in SEQ ID NO: 4 (IB204594R), and the marker comprising the nucleotide sequence as shown in SEQ ID NO: 5 (IB303642R) are reciprocal markers linked to traits that do not exhibit everbearing properties and other markers are coupling markers linked to traits that exhibit everbearing properties. Coupling markers are particularly preferable as the markers associated with everbearing properties in plants of the genus *Fragaria* according to the present invention.

A continuous nucleic acid region in the 5.5-cM region shown in Table 1 can be used as the marker associated with everbearing properties in plants of the genus *Fragaria*. The term "nucleic acid region" used herein refers to a region comprising a nucleotide sequence having 95% or less, preferably 90% or less, more preferably 80% or less, and most preferably 70% or less identity to the other region in the chromosome of the plant of the genus *Fragaria*. As long as the degree of identity between the nucleic acid region as the marker associated with everbearing properties in plants of the genus *Fragaria* and the other region is within the range described above, such nucleic acid region can be specifically detected in accordance with a conventional technique. The degree of identity can be determined using, for example, BLAST with the default parameters.

A nucleic acid region serving as the marker associated with everbearing properties in plants of the genus *Fragaria* can comprise at least 8, preferably 15 or more, more preferably 20 or more, and most preferably 30 nucleotides. As long as the number of nucleotides constituting the nucleic acid region as the marker associated with everbearing properties in plants of the genus *Fragaria* is within such range, such nucleic acid region can be specifically detected in accordance with a conventional technique.

In addition, a marker associated with everbearing properties in plants of the genus *Fragaria* is not limited to a continuous nucleic acid region sandwiched between the nucleotide sequence as shown in SEQ ID NO: 1 and the nucleotide sequence as shown in SEQ ID NO: 5. For example, it may be a continuous nucleic acid region sandwiched between the nucleotide sequence as shown in SEQ ID NO: 1 and the nucleotide sequence as shown in SEQ ID NO: 4, a continuous nucleic acid region sandwiched between the nucleotide sequence as shown in SEQ ID NO: 1 and the nucleotide sequence as shown in SEQ ID NO: 3, a continuous nucleic acid region sandwiched between the nucleotide sequence as shown in SEQ ID NO: 1 and the nucleotide sequence as shown in SEQ ID NO: 2, a continuous nucleic acid region sandwiched between the nucleotide sequence as shown in SEQ ID NO: 2 and the nucleotide sequence as shown in SEQ ID NO: 5, a continuous nucleic acid region sandwiched between the nucleotide sequence as shown in SEQ ID NO: 2 and the nucleotide sequence as shown in SEQ ID NO: 4, a continuous nucleic acid region sandwiched between the nucleotide sequence as shown in SEQ ID NO: 2 and the nucleotide sequence as shown in SEQ ID NO: 3, a continuous nucleic acid region sandwiched between the nucleotide sequence as shown in SEQ ID NO: 3 and the nucleotide sequence as shown in SEQ ID NO: 5, a continuous nucleic acid region sandwiched between the nucleotide sequence as shown in SEQ ID NO: 3 and the nucleotide sequence as shown in SEQ ID NO: 4, or a continuous nucleic acid region sandwiched between the nucleotide sequence as shown in SEQ ID NO: 4 and the nucleotide sequence as shown in SEQ ID NO: 5.

In particular, the marker associated with everbearing properties in plants of the genus *Fragaria* is preferably selected from a region sandwiched between the nucleotide sequence as shown in SEQ ID NO: 3 and the nucleotide sequence as shown in SEQ ID NO: 4 among the 5 types of markers included in the 5.5-cM region because the peak is located in the region sandwiched between the nucleotide sequence as shown in SEQ ID NO: 3 and the nucleotide sequence as shown in SEQ ID NO: 4.

The marker associated with everbearing properties in plants of the genus *Fragaria* can be a nucleic acid region including a single type of marker selected from among the 5 types of markers shown in Table 1. For example, use of a nucleic acid region including a marker comprising the nucleotide sequence as shown in SEQ ID NO: 4 (IB204594R), which is located in a position nearest to the peak, as the marker associated with everbearing properties in plants of the genus *Fragaria* is preferable. In such a case, the nucleotide sequence of the nucleic acid region including the marker can be identified by a method of flank sequence analysis, such as inverse PCR using primers designed based on the nucleotide sequence of the marker.

Alternatively, a plurality of regions may be selected from a nucleic acid region sandwiched between the nucleotide sequence as shown in SEQ ID NO: 1 and the nucleotide sequence as shown in SEQ ID NO: 5 in the chromosome of the plant of the genus *Fragaria* as the marker associated with everbearing properties in the plant of the genus *Fragaria*.

In addition, any of the above 5 types of markers can be directly used as markers associated with everbearing properties in plants of the genus *Fragaria*. Specifically, one or more regions selected from the 5 regions comprising the nucleotide sequences as shown in SEQ ID NOs: 1 to 5 can be used as markers associated with everbearing properties in plants of the genus *Fragaria*. For example, use of a marker comprising the nucleotide sequence as shown in SEQ ID NO: 3 (IBA38559) and/or a marker comprising the nucleotide sequence as shown in SEQ ID NO: 4 (IB204594R), which are/is located in a position (or positions) near the peak, as the marker associated with everbearing properties in plants of the genus *Fragaria* is preferable. Alternatively, use of a marker comprising the nucleotide sequence as shown in SEQ ID NO: 4, which is located in a position nearest to the peak (IB204594R), as the marker associated with everbearing properties in plants of the genus *Fragaria* is more preferable.

[Identification of Marker in Plants of the Genus *Fragaria*]

In the present invention, as described above, the markers associated with everbearing properties in plants of the genus *Fragaria* were identified from among the 8,218 markers acquired from the strawberry variety "Miyazaki Natsu Haruka" and the 8,039 markers acquired from the strawberry line "08 To-f." Such 8,218 markers and 8,039 markers are described below. These markers can be identified with the use of a DNA microarray in accordance with the methods disclosed in JP 2011-120558 A or WO 2011/074510.

Specifically, probes used for the DNA microarray are designed in the manner shown in FIG. 1. That is, genomic DNA is first extracted from "Miyazaki Natsu Haruka" or "08 To-f" (Step 1a). Subsequently, the extracted genomic DNA is digested with one or more restriction enzymes (Step 1b). In an embodiment shown in FIG. 1, two types of restriction enzymes, Restriction enzyme A and Restriction enzyme B, are used in that order to digest genomic DNA. Restriction enzymes are not particularly limited, and examples of restriction enzymes that can be used include PstI, EcoRI, HindIII, BstNI, HpaII, and HaeIII. Restriction enzymes can be adequately selected by taking, for example, the frequency of recognition sequence appearance into consideration, so as to yield a genomic DNA fragment with 20 to 10,000 nucleotides upon complete digestion of genomic DNA. When a plurality of restriction enzymes are used, it is preferable that the genomic DNA fragment comprise 200 to 6,000 nucleotides after all the restriction enzymes are used. When a plurality of restriction enzymes are used, in addition, the order in which restriction enzymes are subjected to treatment is not particularly limited. Under common treatment conditions (e.g., a solution composition or temperature), a plurality of restriction enzymes may be used in the same reaction system. While Restriction enzyme A and Restriction enzyme B are successively used in that order so as to digest genomic DNA in an embodiment shown in FIG. 1, specifically, Restriction enzyme A and Restriction enzyme B may be simultaneously used in the same reaction system to digest genomic DNA. Alternatively, Restriction enzyme B and Restriction enzyme A may be successively used in that order, so as to digest genomic DNA. In addition, 3 or more restriction enzymes may be used.

Subsequently, adaptors are bound to the genomic DNA fragment treated with restriction enzymes (Step 1c). The adaptors used herein are not particularly limited, provided that such adaptors can be bound to the both ends of the genomic DNA fragment obtained through the treatment with restriction enzymes. An example of an adaptor that can be used is an adaptor comprising a single strand that is complementary to a protruding end (a sticky end) formed at both ends of the genomic DNA fragment obtained through the treatment with restriction enzymes and having a primer-binding sequence to which a primer used at the time of amplification can hybridize (details are described below). Alternatively, an adaptor comprising a single strand complementary to the protruding end (a sticky end) and having a restriction enzyme recognition site to be incorporated into a vector at the time of cloning can be used.

When genomic DNA is digested with a plurality of restriction enzymes, a plurality of adaptors corresponding to relevant restriction enzymes can be used. Specifically, a plurality of adaptors each comprising a single strand complementary to any of a plurality of types of protruding ends resulting from digestion of genomic DNA with a plurality of types of restriction enzymes can be used. In such a case, a plurality of adaptors corresponding to a plurality of restriction enzymes may have common primer-binding sequences enabling hybridization of common primers. Alternatively, such adaptors may have different primer-binding sequences, so that different primers can hybridize thereto.

When genomic DNA is digested with a plurality of restriction enzymes, in addition, an adaptor corresponding to a restriction enzyme selected from among the plurality of restriction enzymes used or adaptors corresponding to a subset of restriction enzymes selected from among the plurality of restriction enzymes used can be prepared.

Subsequently, a genomic DNA fragment comprising adaptors bound to both ends thereof is amplified (Step 1d). When adaptors comprising primer-binding sequences are used, primers that can hybridize to such primer-binding sequences may be used, so that the genomic DNA fragment can be amplified. Alternatively, a genomic DNA fragment comprising adaptors added thereto may be cloned into a vector using the adaptor sequences, and primers that can hybridize to particular regions in such vector may be used, so as to amplify the genomic DNA fragment. An example of an amplification reaction of the genomic DNA fragment with the use of primers is PCR.

When genomic DNA is digested with a plurality of restriction enzymes and a plurality of adaptors corresponding to relevant restriction enzymes are ligated to the genomic DNA fragments, adaptors would be ligated to all genomic DNA fragments resulting from the treatment with the plurality of restriction enzymes. In such a case, primer-binding sequences contained in the adaptors may be used to perform a nucleic acid amplification reaction. Thus, all resulting genomic DNA fragments can be amplified.

When genomic DNA is digested with a plurality of restriction enzymes and an adaptor corresponding to a restriction enzyme selected from among the plurality of restriction enzymes used or adaptors corresponding to a subset of restriction enzymes selected from among the plurality of restriction enzymes used are ligated to the genomic DNA fragments, alternatively, the genomic DNA fragments comprising the recognition sequences for the selected restriction enzymes at both ends thereof can be selectively amplified among the resulting genomic DNA fragments.

Subsequently, nucleotide sequences of the amplified genomic DNA fragments are determined (Step 1e), one or more regions of a nucleotide length shorter than that of the genomic DNA fragment and corresponding to at least a part of the genomic DNA fragment are identified, and the one or more identified regions are designed as probes in strawberry cultivars (Step 1f). A method for determining nucleotide sequences of genomic DNA fragments is not particularly limited. For example, a conventional technique involving the use of a DNA sequencer in accordance with the Sanger's method can be employed. A region to be designed herein is of, for example, a 20- to 100-nucleotide length, preferably a 30- to 90-nucleotide length, and more preferably a 50- to 75-nucleotide length, as described above.

As described above, many probes are designed using genomic DNAs extracted from strawberry cultivars, and oligonucleotides comprising target nucleotide sequences are synthesized on a support based on the nucleotide sequences of the designed probes. Thus, a DNA microarray can be produced. With the use of the DNA microarray produced as described above, the 8,218 markers and the 8,039 markers including the 5 types of markers associated with everbearing properties in plants of the genus *Fragaria* as shown in SEQ ID NOs: 1 to 5 can be identified.

More specifically, the present inventors obtained the signal data with the use of the DNA microarray concerning 8,215 markers obtained from the strawberry variety "Miyazaki Natsu Haruka," the strawberry line "08 To-f," and hybrid progeny lines thereof (147 lines). They then obtained the genotype data from the obtained signal data, and, on the basis of the obtained genotype data, they obtained the positional information for markers in the chromosomes in accordance with a genetic distance calculation formula (Kosambi) using genetic map production software (AntMap, Iwata, H., Ninomiya, S., 2006, AntMap: Constructing genetic linkage maps using an ant colony optimization algorithm. Breed Sci., 56: 371-378). On the basis of the positional information for the obtained markers, in addition, a genetic map datasheet was prepared using the Mapmaker/EXP ver. 3.0 (A Whitehead Institute for Biomedical Research Technical Report, Third Edition, January, 1993). As a result, the 8,218 markers and the 8,039 markers including the 5 types of markers associated with everbearing properties in plants of the genus *Fragaria* as shown in SEQ ID NOs: 1 to 5 are identified.

[Use of Markers Associated with Everbearing Properties in Plants of the Genus *Fragaria*]

With the use of the markers associated with everbearing properties in plants of the genus *Fragaria*, whether or not plants of the genus *Fragaria* whose everbearing properties remain unknown (e.g., progeny lines) have everbearing properties can be determined. The use of markers associated with everbearing properties in plants of the genus *Fragaria* includes an embodiment of the use of a method that specifically amplifies a nucleic acid fragment comprising the markers and an embodiment of the use of a DNA microarray comprising probes corresponding to the markers.

The method that specifically amplifies a nucleic acid fragment comprising markers associated with everbearing properties in plants of the genus *Fragaria* is a method of so-called nucleic acid amplification. Examples of methods of nucleic acid amplification include a method involving the use of a primer designed so as to specifically amplify a target nucleic acid fragment and a method of specifically amplifying a target nucleic acid fragment without the use of a primer.

A primer that specifically amplifies a target nucleic acid fragment is an oligonucleotide that can amplify a nucleic acid fragment comprising a marker associated with everbearing properties in plants of the genus *Fragaria* as defined above by a method of nucleic acid amplification. Methods of nucleic acid amplification involving the use of primers are not particularly limited, and any method may be employed, provided that a nucleic acid fragment is amplified. A representative example is a polymerase chain reaction (PCR). Examples of other methods include, but are not limited to, conventional techniques, such as rolling circle amplification (RCA), cycling probe technology (CPT), isothermal and chimeric-primer-initiated amplification of nucleic acids (ICAN), loop-mediated isothermal amplification of DNA (LAMP), strand displacement amplification (SDA), nucleic-acid-sequence-based amplification (NASBA), and transcription-mediated amplification (TMA).

When PCR is selected from among such nucleic acid amplification reactions, for example, a pair of primers are designed so as to sandwich markers associated with everbearing properties in plants of the genus *Fragaria* in the chromosome of the plant of the genus *Fragaria*. When the LAMP method is employed, 4 types of primers are designed so as to sandwich the markers associated with everbearing properties in plants of the genus *Fragaria* in the chromosome of plants of the genus *Fragaria*.

A method of nucleic acid amplification to be performed without the use of a primer is not particularly limited, and an example thereof is a method of ligase chain reaction (LCR). When the method of LCR is employed, a plurality of oligonucleotides that hybridize to nucleic acid fragments containing the markers associated with everbearing properties in plants of the genus *Fragaria* are designed.

When the markers associated with everbearing properties in plants of the genus *Fragaria* are present in the target plants of the genus *Fragaria*, as described above, nucleic acid fragments containing the markers can be obtained as amplification products according to methods of nucleic acid amplification. When a nucleic acid fragment of interest is amplified via a method of nucleic acid amplification using, as a template, the chromosome extracted from the target plant of the genus *Fragaria*, in other words, the target plant of the genus *Fragaria* can be determined to have everbearing properties.

Methods for detecting an amplified nucleic acid fragment are not particularly limited. Examples thereof include a method in which a solution resulting after the amplification reaction is subjected to agarose electrophoresis, and a fluorescent intercalator, such as ethidium bromide or SYBR green, is allowed to bind thereto, so as to observe specific fluorescence, a method in which a fluorescent intercalator is added to a solution used for nucleic acid amplification, so as to detect fluorescence after the amplification reaction, and a method in which nucleic acid amplification is carried out with the use of a fluorescence-labeled primer, so as to detect fluorescence after the amplification reaction.

When the markers associated with everbearing properties in plants of the genus *Fragaria* are detected via a method of nucleic acid amplification, an amplified fragment containing such markers can contain, for example, 30 to 10.000, preferably 50 to 5,000, and more preferably 70 to 2,000 nucleotides, although the number of nucleotides would vary depending on the principle of the method of nucleic acid amplification.

When evaluating the everbearing properties in plants of the genus *Fragaria*, a plurality of markers associated with everbearing properties in plants of the genus *Fragaria* may be detected. Specifically, a plurality of regions selected from nucleic acid regions sandwiched between the nucleotide sequence as shown in SEQ ID NO: 1 and the nucleotide sequence as shown in SEQ ID NO: 5 in the chromosome of plants of the genus *Fragaria* may be designated as the markers associated with everbearing properties in plants of the genus *Fragaria*, and the plurality of markers associated with everbearing properties in plants of the genus *Fragaria* may be detected. For example, a plurality of regions selected from among 5 regions consisting of nucleotide sequences as shown in SEQ ID NOs: 1 to 5 may be designated as the markers associated with everbearing properties in plants of the genus *Fragaria*, and the plurality of regions may be detected.

For example, the region comprising the nucleotide sequence as shown in SEQ ID NO: 3 (IBA38559) and the region comprising the nucleotide sequence as shown in SEQ ID NO: 4 (IB204594R) may be designated as the markers associated with everbearing properties in plants of the genus *Fragaria*, and these regions may be subjected to nucleic acid amplification, so as to determine the presence or absence of the markers associated with everbearing properties in plants of the genus *Fragaria*. Alternatively, a region sandwiched between the region comprising the nucleotide sequence as shown in SEQ ID NO: 2 (IBA38559) and the region comprising the nucleotide sequence as shown in SEQ ID NO: 4 (IB204594R) may be designated as the marker associated with everbearing properties in plants of the genus *Fragaria*, and the region may be subjected to nucleic acid amplification, so as to determine the presence or absence of the marker associated with everbearing properties in plants of the genus *Fragaria*.

According to an embodiment in which a DNA microarray comprising probes corresponding to the markers associated with everbearing properties in plants of the genus *Fragaria* is used, the probes are oligonucleotides that can hybridize specifically to the markers associated with everbearing properties in plants of the genus *Fragaria* as defined above under stringent conditions. Such an oligonucleotide can be designed as, for example, a partial region comprising 10, 15, 20, 25, 30, 35, 40, 45, 50, or more continuous nucleotides in the nucleotide sequence of the marker associated with everbearing properties in plants of the genus *Fragaria* as defined above or a complementary strand thereof or the entire region of the nucleotide sequence. The DNA microarray comprising probes may be, for example, a microarray comprising a planar substrate of glass or silicone as a carrier, a bead array comprising microbeads as carriers, or a three-dimensional microarray comprising probes immobilized on the inner wall of a hollow fiber.

With the use of the DNA microarray thus produced, whether or not a plant of the genus *Fragaria* whose phenotypic characteristics with regard to everbearing properties remain unknown (e.g., a progeny line) exhibits a phenotype indicating excellent everbearing properties can be determined. Alternatively, the marker associated with everbearing properties in plants of the genus *Fragaria* may be detected in accordance with a conventional technique, and whether or not the target plants of the genus *Fragaria* have excellent everbearing properties may be determined by a method other than the method involving the use of a DNA microarray. An example of a method other than the method involving the use of a DNA microarray that can be employed is so-called FISH (fluorescence in situ hybridization) involving the use of the probes described above.

Figure 2:
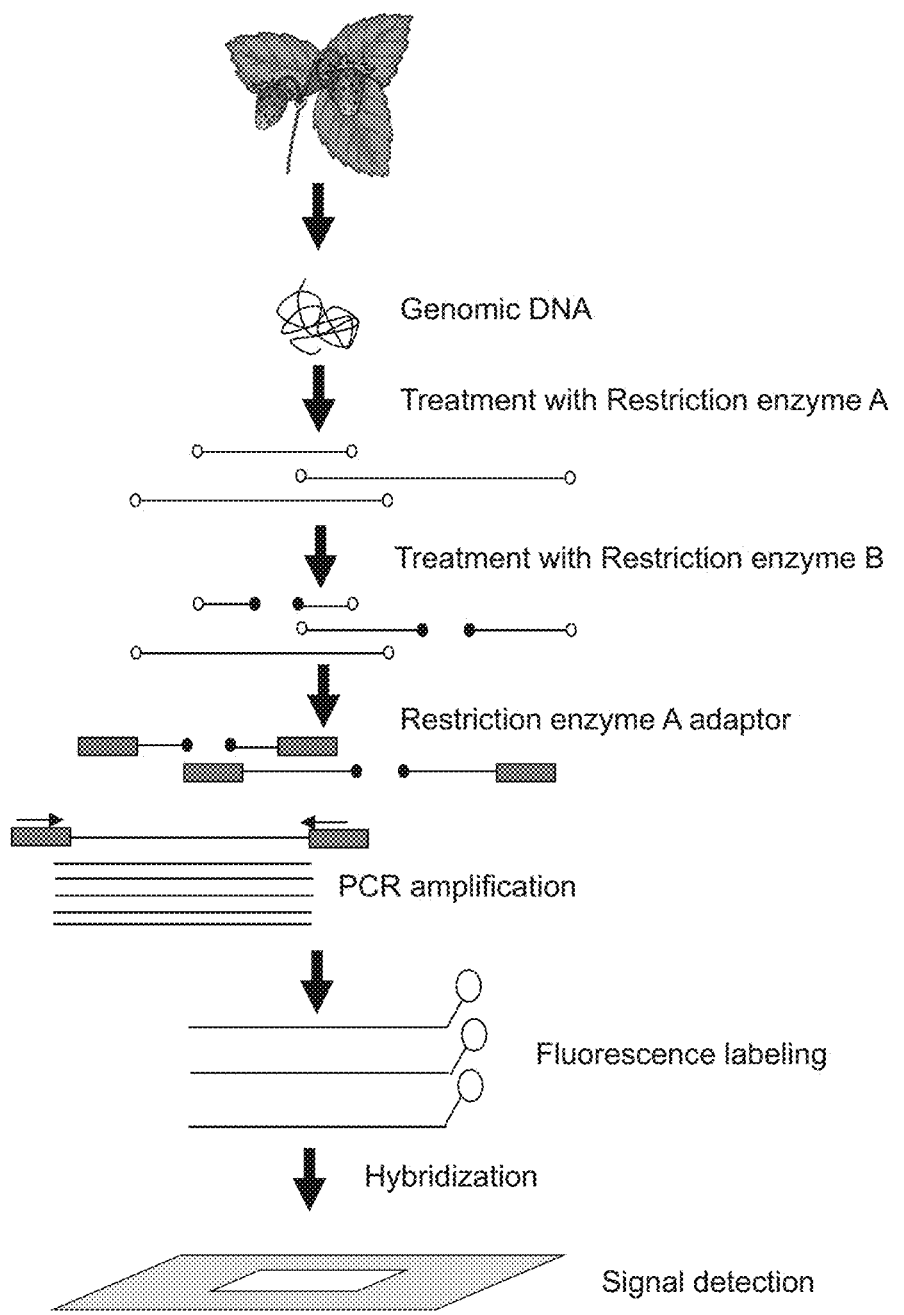
FIG. 2 schematically shows a step of signal detection using a DNA microarray.

A method involving the use of a DNA microarray is described in greater detail. As shown in FIG. 2, genomic DNA is first extracted from a target plant of the genus *Fragaria*. A target plant of the genus *Fragaria* is a plant of the genus *Fragaria* whose phenotypic characteristics with regard to everbearing properties remain unknown (e.g., a progeny line) and/or a parent plant of the genus *Fragaria* used when producing a progeny line, which is to be evaluated as to trains of excellent everbearing properties.

Subsequently, the extracted genomic DNA is digested with the restriction enzyme used when preparing the DNA microarray described in the [Identification of markers in plants of the genus *Fragaria*] section above, so as to prepare a plurality of genomic DNA fragments. The resulting genomic DNA fragments are then ligated to adaptors used when preparing the DNA microarray. The genomic DNA fragments comprising adaptors added to the both ends are then amplified using the primers used when preparing the DNA microarray. Thus, the genomic DNA fragments derived from the target plant of the genus *Fragaria* corresponding to the genomic DNA fragment amplified in Step 1d when preparing a DNA microarray can be amplified.

In this step, among the genomic DNA fragments comprising adaptors added thereto, specific genomic DNA fragments may be selectively amplified. When a plurality of adaptors corresponding to the plurality of restriction enzymes are used, for example, genomic DNA fragments comprising specific adaptors added thereto can be selectively amplified. When genomic DNA is digested with a plurality of restriction enzymes, adaptors are selectively added to the genomic DNA fragments having protruding ends corresponding to specific restriction enzymes among the resulting genomic DNA fragments. Thus, genomic DNA fragments comprising the adaptors added thereto can be selectively amplified. By selectively amplifying specific genomic DNA fragments, as described above, these fragments can be concentrated.

Subsequently, the amplified genomic DNA fragments are labeled. Any conventional material may be used as a label. Examples of labels that can be used include fluorescent molecules, pigment molecules, and radioactive molecules. This step can be omitted with the use of a labeled nucleotide in the step of genomic DNA fragment amplification. That is, a genomic DNA fragment is amplified with the use of a labeled nucleotide in the above step, so that the amplified DNA fragment is labeled.

Subsequently, a labeled genomic DNA fragment is brought into contact with a DNA microarray under given conditions, so as to allow a probe immobilized on a DNA microarray to hybridize to the labeled genomic DNA fragment. It is preferable that hybridization be carried out under highly stringent conditions. Under highly stringent conditions, whether or not the marker associated with everbearing properties in plants of the genus *Fragaria* is present in the target plant of the genus *Fragaria* can be determined with higher accuracy. Stringent conditions can be adjusted based on reaction temperature and salt concentration. Specifically, higher stringency can be realized by increasing temperature or decreasing salt concentration. When a probe comprising 50 to 75 nucleotides is used, for example, hybridization can be carried out at 40° C. to 44° C. in 0.2% SDS and 6×SSC, so that higher stringency can be realized.

Hybridization between a probe and a labeled genomic DNA fragment can be detected based on a label. After the hybridization reaction between the labeled genomic DNA fragment and the probes, specifically, unreacted genomic DNA fragments or the like are washed, and a label bound to the genomic DNA fragment that had specifically hybridized to the probes are then observed. In the case that the label is a fluorescent material, for example, the fluorescent wavelength thereof is detected. When a label is a pigment molecule, the pigment wavelength thereof is detected. More specifically, apparatuses such as fluorescence detectors or image analyzers used for conventional DNA microarray analysis can be used.

By the method involving nucleic acid amplification or the method involving the use of a DNA microarray, as described above, whether or not the target plant of the genus *Fragaria* has the marker associated with everbearing properties in plants of the genus *Fragaria* can be determined. As described above, a marker associated with everbearing properties in a plant of the genus *Fragaria* is linked to traits of everbearing properties. If a marker associated with everbearing properties in a plant of the genus *Fragaria* is present, accordingly, the target plant can be determined as an everbearing line or variety.

According to the method described above, in particular, it is not necessary to have the target plant of the genus *Fragaria* subjected to the test as to everbearing properties. For example, seeds of progeny lines or young seedlings germinated from such seeds can be used. With the use of the markers associated with everbearing properties in plants of the genus *Fragaria*, accordingly, cost of the field for growing the target plant of the genus *Fragaria* and cost for growing the plant can be reduced to a significant extent. Also, the use of markers associated with everbearing properties in plants of the genus *Fragaria* eliminates the need to inspect whether or not floral buds are actually formed under high-temperature and long-day conditions. Thus, expenditures required for equipment such as a large-scale greenhouse for an exclusive purpose, a field for an exclusive purpose, or a facility isolated from the outside can be reduced.

When producing new varieties of the plants of the genus *Fragaria*, it is particularly preferable that several tens of thousands of types of hybrid species be first produced via crossing and evaluation take place prior to or instead of seedling selection with the use of the markers associated with everbearing properties in plants of the genus *Fragaria*. Thus, the number of plants to be grown in the actual field can be reduced to a significant extent, and the labor and expenditures required for the production of new varieties of plants of the genus *Fragaria* can be reduced to a significant extent.

When producing new varieties of plants of the genus *Fragaria*, alternatively, the presence or absence of the markers associated with everbearing properties in plants of the genus *Fragaria* in the parent varieties to be used for crossing is first evaluated, and parent varieties with excellent everbearing properties can be selected. By producing progeny lines with the preferential use of parent varieties with excellent everbearing properties, progeny lines with excellent everbearing properties can develop at high frequency. Thus, the number of plants necessary to cultivate in order to produce superior lines can be reduced to a significant extent, and the labor and expenditures required for the production of new plant varieties of the genus *Fragaria* can be reduced to a significant extent.

Examples

Hereafter, the present invention is described in greater detail with reference to the examples, although the technical scope of the present invention is not limited to these examples.

1. Preparation of DNA Microarray Probe
(1) Materials
The strawberry varieties: "Miyazaki Natsu Haruka" and "08 To-f," were used.
(2) Treatment with Restriction Enzyme
Genomic DNA was extracted from these strawberry varieties using the Dneasy Plant Mini Kit (Qiagen). The extracted genomic DNA (150 ng) was treated with the PstI restriction enzyme (5 units, NEB) at 37° C. for 1 hour.
(3) Ligation of Adaptors
The PstI sequence adaptors (5'-CACGATGGATCCAGT-GCA-3' (SEQ ID NO: 6) and 5'-CTGGATCCATCGTGCA-3' (SEQ ID NO: 7)) and T4 DNA ligase (200 units, NEB) were added to the genomic DNA fragment (150 ng) treated in (2) above, and the resultant was subjected to ligation at 16° C. for 1 hour, 55° C. for 20 minutes, and then 37° C. for 30 minutes. Subsequently, the BstNI restriction enzyme (6 units, NEB) was added to the treated sample, and the sample was then treated at 60° C. for 1 hour.

(4) Amplification by PCR

The PstI sequence adaptor recognition primer (5'-GATG-GATCCAGTGCAG-3' (SEQ ID NO: 8)) and Taq polymerase (1.25 units, PrimeSTAR, Takara Bio Inc.) were added to the sample treated with the BstNI restriction enzyme (15 ng) obtained in (3) above, and the DNA fragment was amplified by PCR (30 cycles of 98° C. for 10 seconds, 55° C. for 15 seconds, and 72° C. for 1 minute, and treatment at 72° C. for 3 minutes, followed by storage at 4° C.).

(5) Acquisition of Genome Sequence

The nucleotide sequence information of the genomic DNA fragment amplified by PCR in (4) above was determined using Hiseq 2000 (Miseq, Illumina).

(6) Design of Probes and Preparation of DNA Microarray

On the basis of the genome sequence information acquired in (5) above, 50 to 60 bp probes were designed. On the basis of the nucleotide sequence information of the designed probes, a DNA microarray comprising these probes was produced.

2. Acquisition of Signal Data (1) Materials

The strawberry varieties: "Miyazaki Natsu Haruka" and "08 To-f," and 147 hybrid progeny lines thereof were used.

(2) Treatment with Restriction Enzyme

Genomic DNA was extracted from these strawberry varieties and the hybrid progeny lines using the Dneasy Plant Mini Kit (Qiagen). The extracted genomic DNA (150 ng) was treated with the PsiI restriction enzyme (6 units, NEB) at 37° C. for 1 hour.

(3) Ligation of Adaptors

The PstI sequence adaptors (5'-CACGATGGATCCAGT-GCA-3' (SEQ ID NO: 6) and 5'-CTGGATCCATCGTGCA-3' (SEQ ID NO: 7)) and T4 DNA ligase (200 units. NEB) were added to the genomic DNA fragment (150 ng) treated in (2) above, and the resultant was subjected to ligation at 16° C. for 1 hour, 55° C. for 20 minutes, and then 37° C. for 30 minutes. Subsequently, the BstNI restriction enzyme (6 units, NEB) was added to the treated sample, and the sample was then treated at 60° C. for 1 hour.

(4) Amplification by PCR

The PstI sequence adaptor recognition primer (5'-GATG-GATCCAGTGCAG-3' (SEQ ID NO: 8)) and Taq polymerase (1.25 units, PrimeSTAR, Takara Bio Inc.) were added to the sample treated with the BstNI restriction enzyme (15 ng) obtained in (3) above, and the genomic DNA fragment was amplified by PCR (30 cycles of 98° C. for 10 seconds, 55° C. for 15 seconds, and 72° C. for 1 minute, and treatment at 72° C. for 3 minutes, followed by storage at 4° C.).

(5) Labeling

The DNA fragment amplified in (4) above was purified through a column (Qiagen), and a labeled sample was then prepared using a NimbleGen One-Color DNA Labeling kit (Roche Diagnostics K.K.) in accordance with the NimbleGen Arrays User's Guide.

(6) Hybridization and Signal Detection

Hybridization was carried out by the array CGH (aCGH) method involving the use of the Agilent in-situ oligo DNA microarray kit using the labeled sample obtained in (5) above and the DNA microarray prepared in 1. above. Signals from the samples were detected.

3. Identification of QTL Associated with Everbearing Properties in Strawberries and Selection of Selection Markers (1) Preparation of Gene Map Data Sheet From the signal data of the 147 hybrid progeny lines of "Miyazaki Natsu Haruka" and "08 To-f," the genotype data of "Miyazaki Natsu Haruka"-type 8,218 markers and "08 To-f"-type 8,039 markers were obtained. On the basis of the genotype data, the gene mapping data of the markers were obtained in accordance with the genetic distance calculation formula (Kosambi) using the genetic map production software (AntMap, Iwata. H., Ninomiya, S., 2006, AntMap: Constructing genetic linkage maps using an ant colony optimization algorithm, Breed Sci. 56: 371-378).

(2) Acquisition of Phenotype Data of Everbearing Properties in Strawberries

Figure 3:
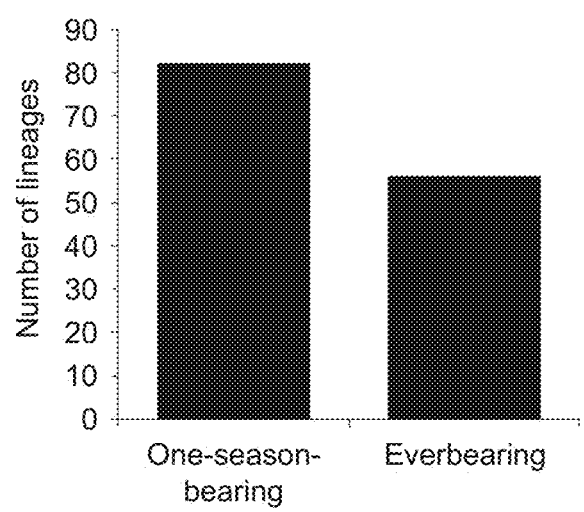
FIG. 3 shows a characteristic diagram showing the results of inspection concerning everbearing properties in hybrid progeny lines of the "Miyazaki Natsu Haruka" and "08 To-f."

The 147 hybrid progeny lines of "Miyazaki Natsu Haruka" and "08 To-f" were cultivated in a greenhouse at a minimal temperature of 17° C. under the 24-hour photoperiod conditions, and the occurrence of flowering was inspected to evaluate the seasonality (FIG. 3). Plants that had formed floral buds under the experimental conditions described above were evaluated as "everbearing strawberries" and those that had not formed floral buds were evaluated as "one-season-bearing strawberries."

(3) Analysis of Quantitative Trait Loci (QTL)

On the basis of the genetic map data obtained in (1) above and the results of everbearing property test obtained in (2) above, QTL analysis was carried out by the composite interval mapping (CIM) method with the use of the genetic analysis software (QTL Cartographer, Wang S., C. J. Basten, and Z.-B. Zeng, 2010, Windows QTL Cartographer 2.5. Department of Statistics, North Carolina State University, Raleigh, N.C.). The LOD threshold was designated to be 2.5. As a result, the presence of the gene associated with everbearing properties in strawberries (LOD value: 7.3) was detected in a region between the IB303507R marker and the IB303642R marker in the 20th linkage group of "Miyazaki Natsu Haruka" (Table 2, FIG. 4).

(4) Selection of Selection Marker

Figure 4:
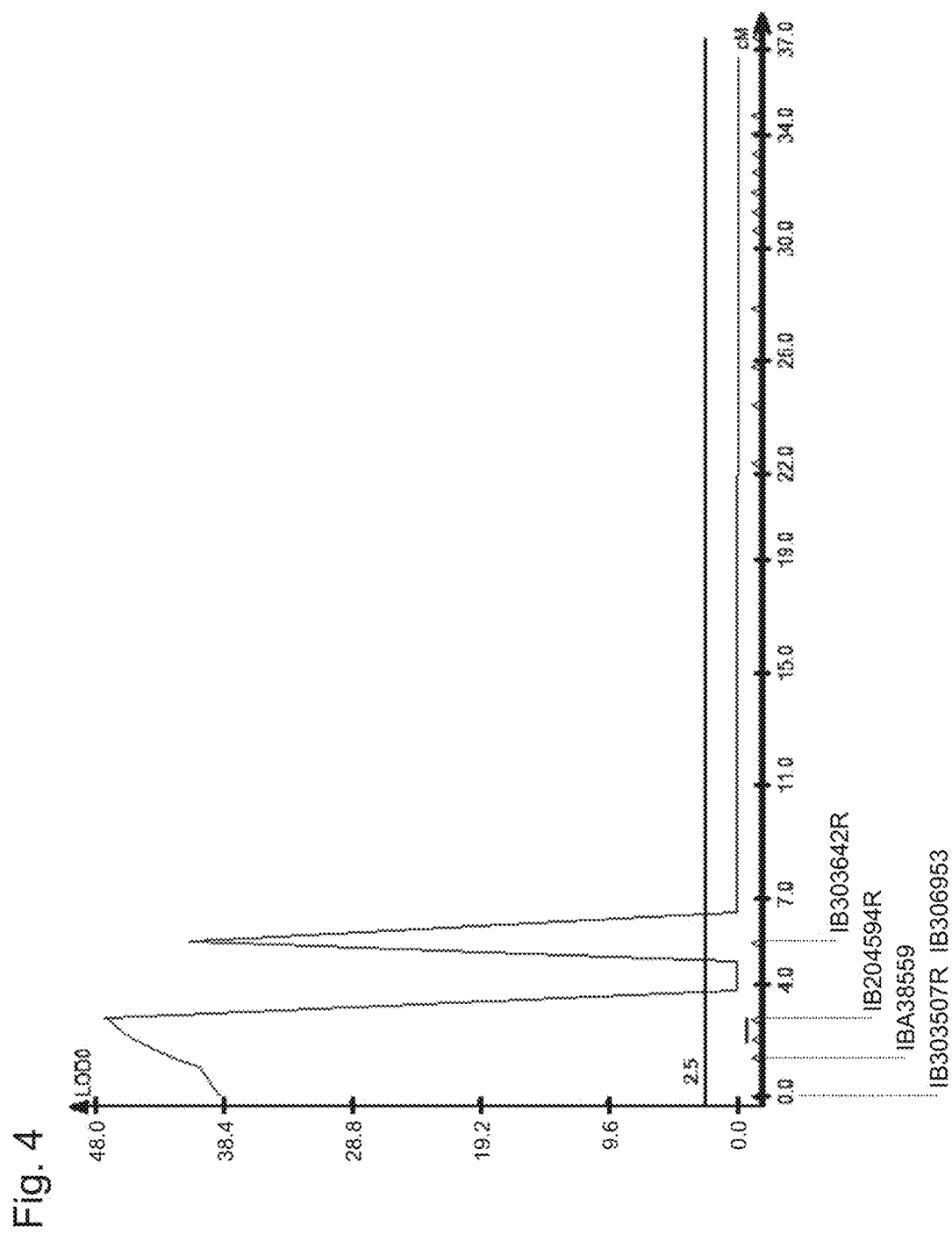
FIG. 4 shows a characteristic diagram showing the results of QTL analysis concerning everbearing properties (the 20th linkage group of "08 To-f").
Figure 7:
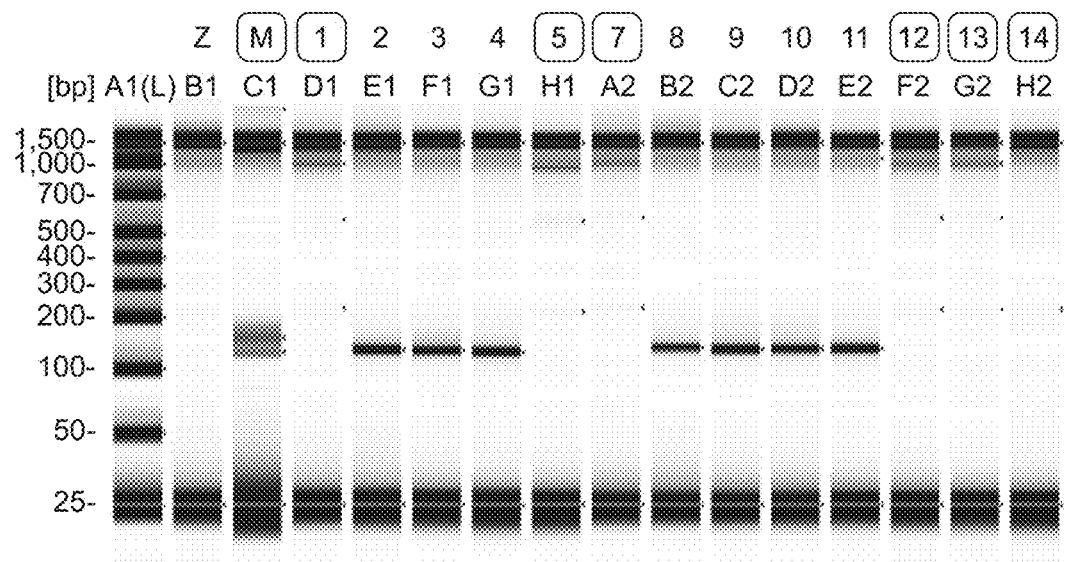
Figure 1:
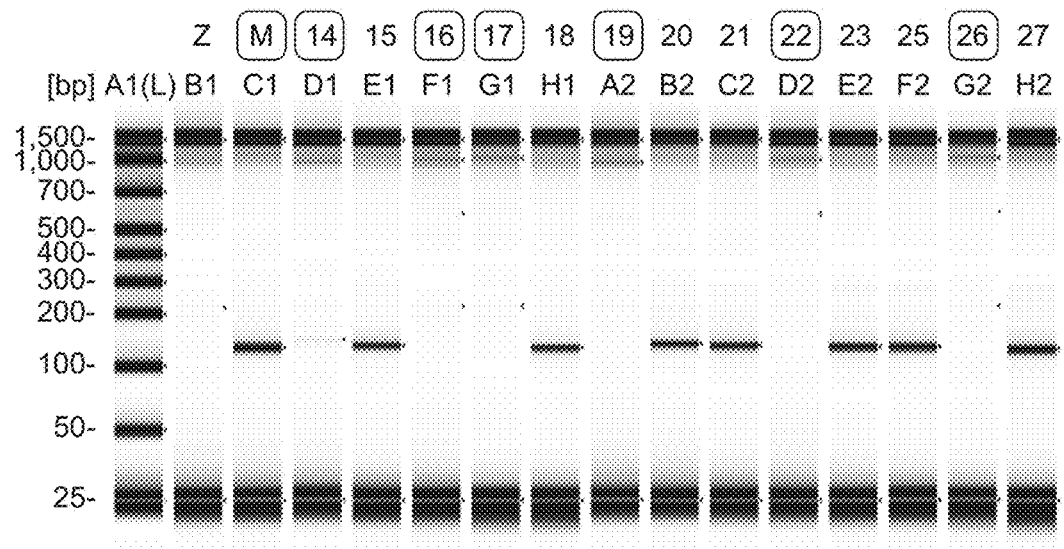
Figures 2, 7:
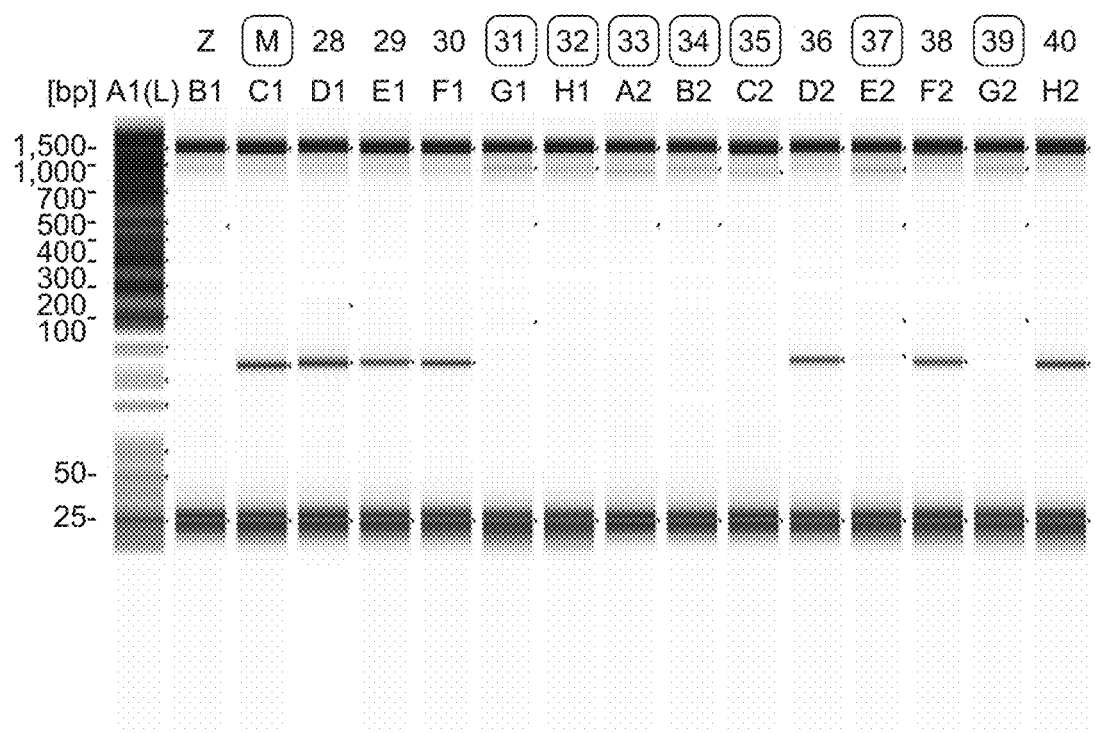
Figure 8:
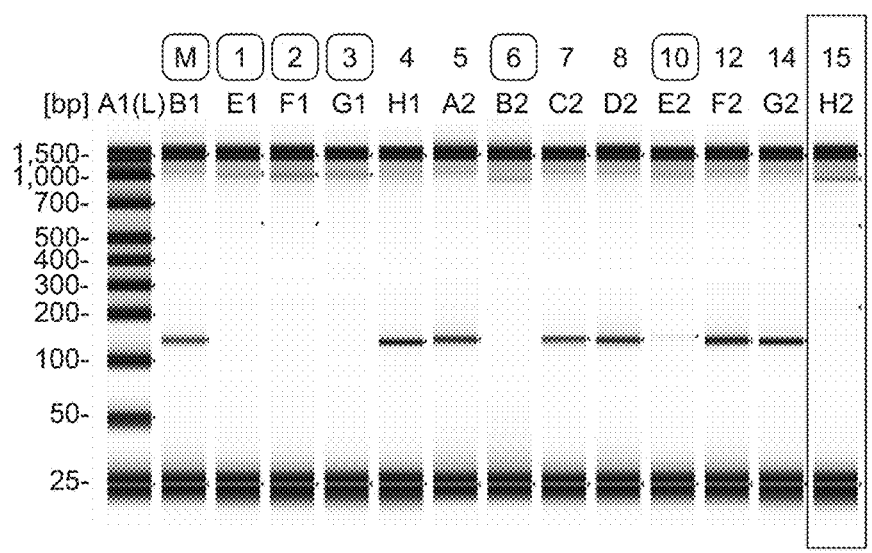
Figure 1:
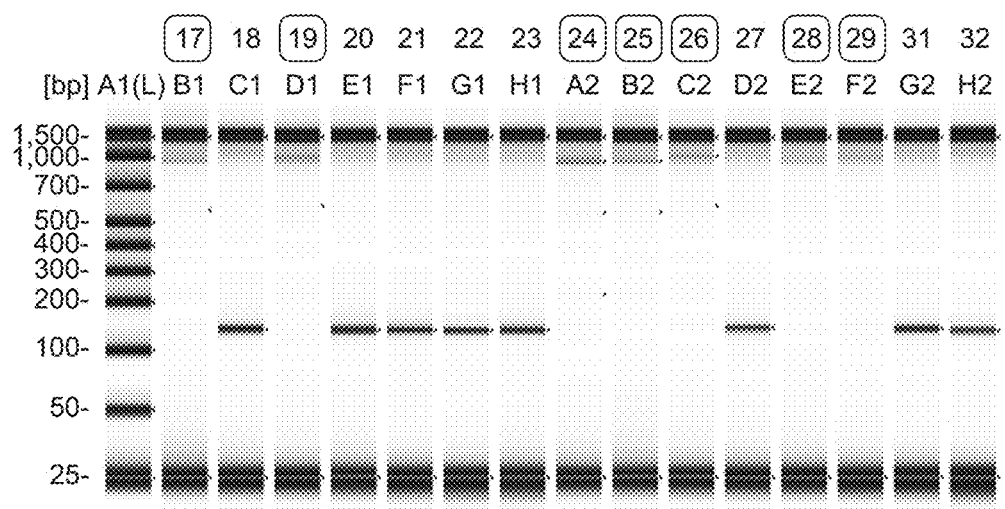
Figures 2, 8:
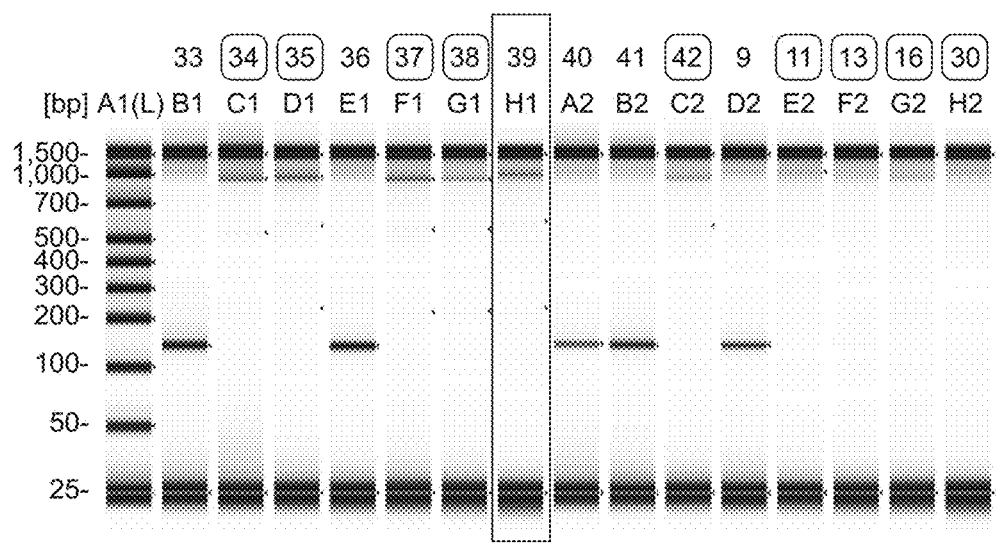
Figures 1, 10:
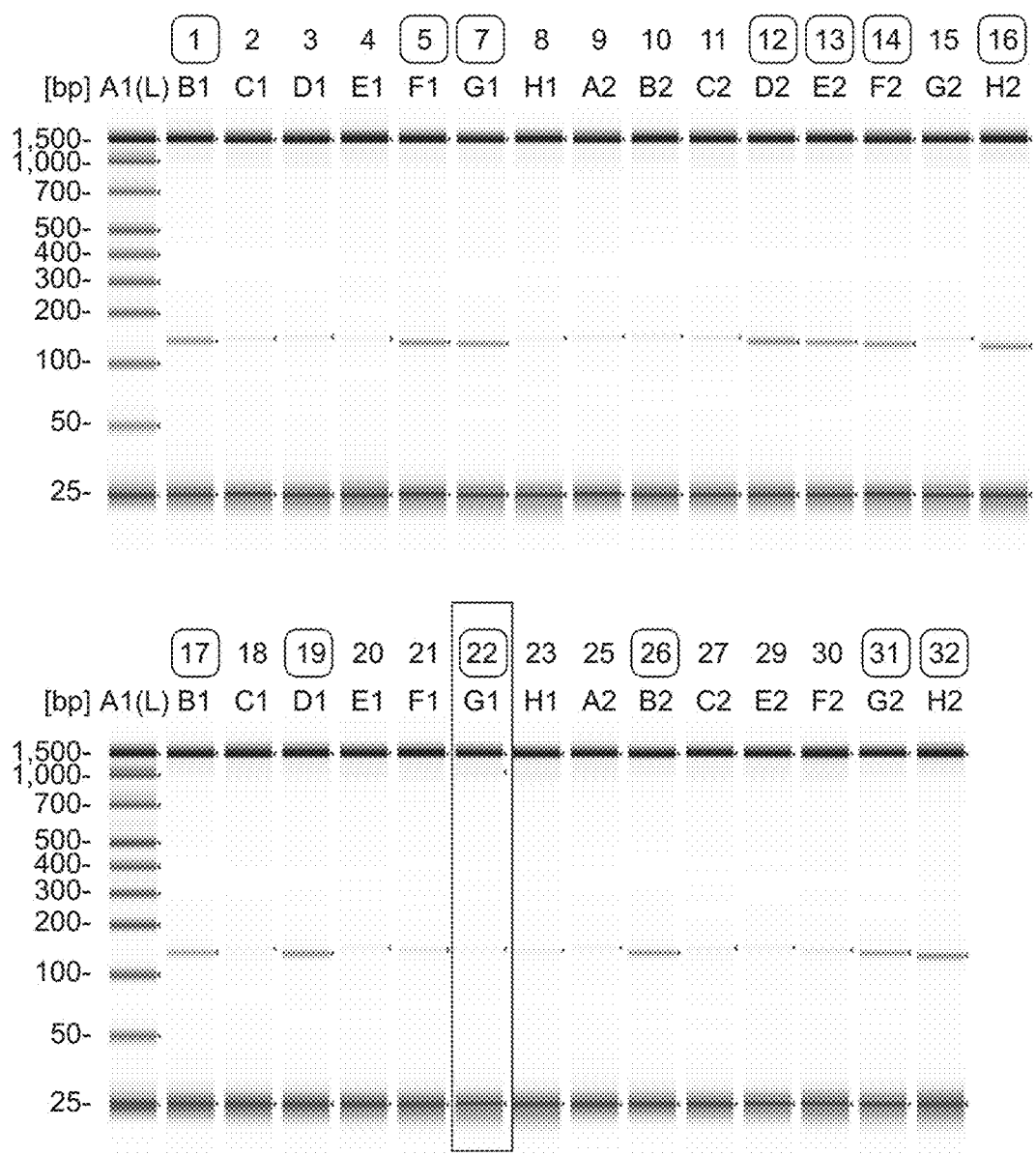
Figure 10:
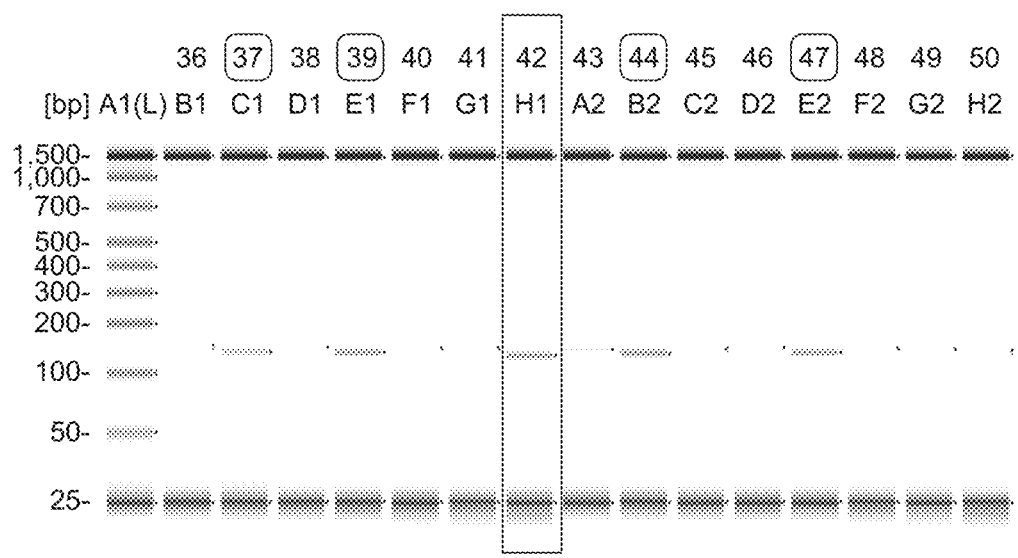
Figure 2:
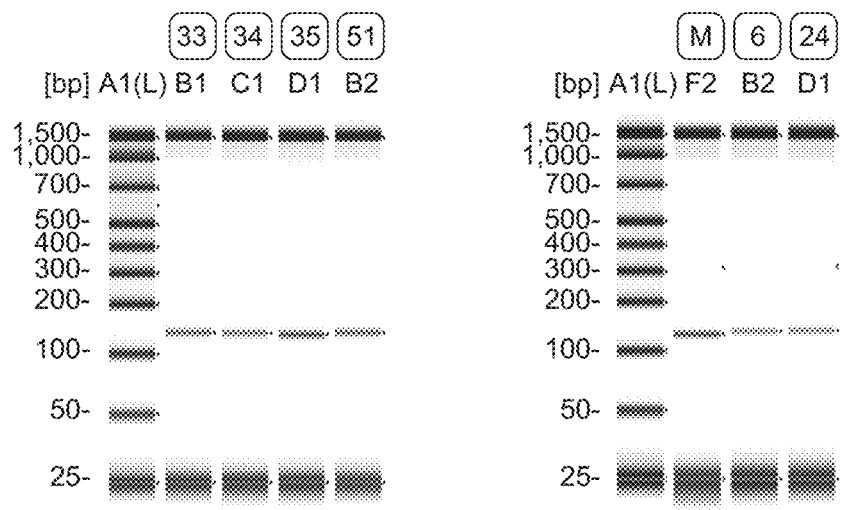
Figures 1, 11:
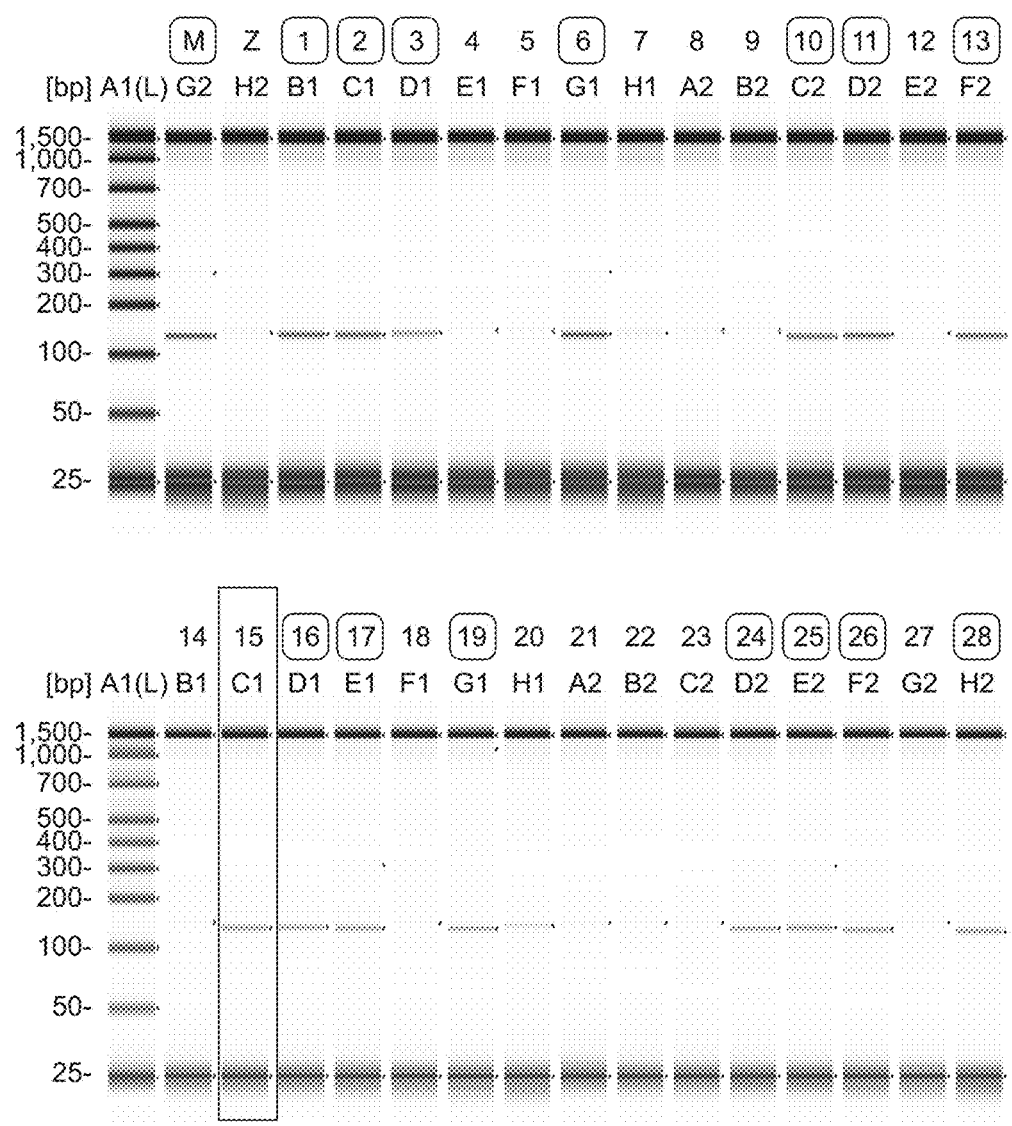
Figures 2, 11:
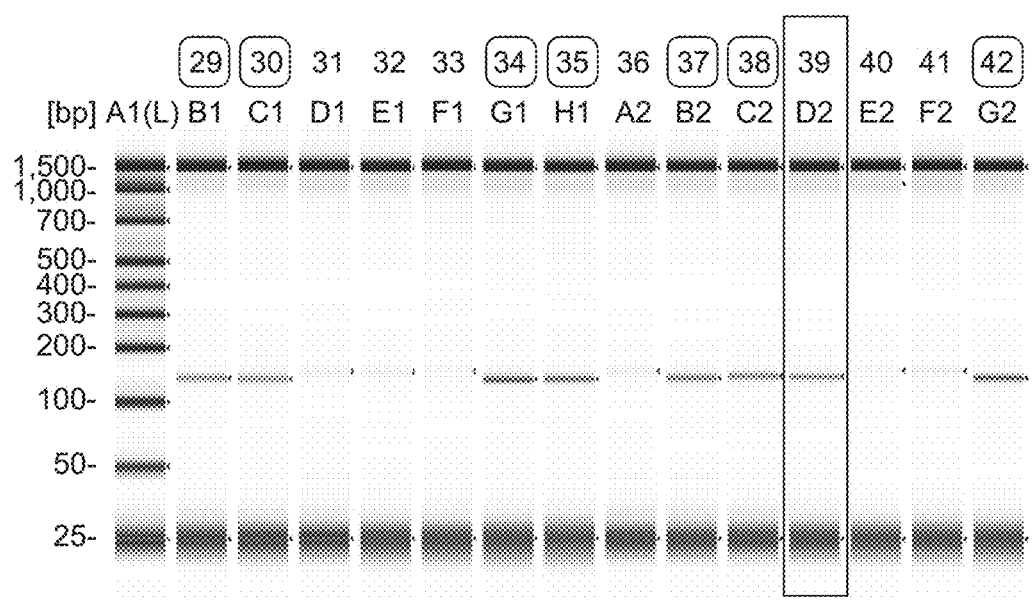

Markers in the vicinity of the region of the gene associated with everbearing properties in strawberries in a region from 0 cM to 5.45 cM of the 20th linkage group were selected as selection markers (FIG. 4, Table 1).

TABLE 2

| Variety | Linkage group | Position (cM) | Range (cM) | Flanking marker | LOD value | Effect* | Contribution rate (%) |
|---|---|---|---|---|---|---|---|
| Miyazaki Natsu Haruka | 20 | 2.7 | 5.5 | IB303507R-IB303642 | 47.4 | 0.9 | 74.8 |

*Everbearing capacity (1: everbearing; 0: one-season-bearing)

In Table 2, the column of the effects indicates an influence of the gene linked to the marker on seasonality (1: everbearing; 0: one-season-bearing). If the numeral value indicating the effects is a positive value, specifically, the gene is altered, so that the strawberry exhibits everbearing properties.

As shown in FIG. 4, a marker located in the vicinity of such peak is inherited in linkage with a causal gene (or causal genes) associated with expression of everbearing properties. This indicates that such marker may be used as the marker associated with everbearing properties in plants of the genus *Fragaria*. Specifically, the 5 types of markers shown in FIG. 4 were found to be usable as the markers associated with everbearing properties in plants of the genus *Fragaria*.

4. Selection of Unknown Line (1) Acquisition of Phenotype Data of Everbearing Properties in Strawberries Separately from the lines described in "3. (2) Acquisition of phenotype data of everbearing properties in strawberries" above, seeds of the hybrid progeny lines of "Miyazaki Natsu Haruka" and "08 To-f" were grown to seedlings in a greenhouse (50 lines, referred to as "Population A"), the resulting seedlings were transplanted in an outdoor field in autumn, and the seasonality was inspected under the natural photoperiodic conditions in the following summer. Also, seeds of the hybrid progeny lines of "Miyazaki Natsu Haruka" and "Ohkimi" (42 lines, referred to as "Population B") were grown to seedlings, transplanted, and then inspected in terms of the seasonality under the natural photoperiodic conditions in the following summer (FIGS. 5-1 and 5-2).

(2) Extraction of Genomic DNA

Separately, genomic DNAs were extracted from the strawberry varieties: "Miyazaki Natsu Haruka" and "08 To-f," and Population A, respectively, using the Dneasy Plant Mini Kit (Qiagen).

(3) Treatment with Restriction Enzyme and Ligation of Adaptors

The extracted genomic DNA (150 ng) was treated with the PstI restriction enzyme (5 units, NEB) at 37° C. for 1 hour, the PstI sequence adaptors (5'-CACGATGGATCCA-GTGCA-3' (SEQ ID NO: 6) and 5'-CTGGATCCATCGT-GCA-3' (SEQ ID NO: 7)) and T4 DNA ligase (200 units. NEB) were added to the sample treated with PsiI, and the resultant was subjected to the treatment at 16° C. for 1 hour, 55° C. for 20 minutes, and then 37° C. for 30 minutes. The BstNI restriction enzyme (6 units. NEB) was added to the treated sample, and the sample was then treated at 60° C. for 1 hour.

(4) Amplification of DNA Fragment

The PsiI sequence adaptor recognition primer (5'-GATG-GATCCAGTGCAG-3' (SEQ ID NO: 8)) and Taq polymerase (1.25 units, PrimeSTAR, Takara Bio Inc.) were added to the sample treated with the BstNI restriction enzyme (15 ng) obtained in (3) above, and the DNA fragment was amplified by PCR (30 cycles of 98° C. for 10 seconds, 55° C. for 15 seconds, and 72° C. for 1 minute, and treatment at 72° C. for 3 minutes, followed by storage at 4° C.).

(5) Labeling

The DNA fragment amplified in (4) above was purified through a column (Qiagen), and a labeled sample was then prepared using a NimbleGen One-Color DNA Labeling kit (Roche Diagnostics K.K.) in accordance with the Nimble-Gen Arrays User's Guide.

(6) Hybridization and Signal Detection

Hybridization was carried out by the array CGH (aCGH) method involving the use of the Agilent in-situ oligo DNA microarray kit using the fluorescence-labeled sample obtained in (5) above and the array prepared in 1. above. Signals from the samples were detected.

(7) Test of Selection Marker

In Population A, the markers in the vicinity of the region of the gene associated with everbearing properties in strawberries were selected (Table 1), the array signal values regarding the selection markers and the phenotypes of Population A were compared, and the degrees of consistency were found to be 92.0% to 98.0% (FIGS. 6-1 to 6-3). In FIGS. 6-1 to 6-3, high array signal values were underlined. The results indicate that the use of the markers shown in Table 1 enables selection of everbearing lines and one-season-bearing lines.

5. Selection and Test Using PCR Base Marker 1

(1) Extraction of Genomic DNA

Genomic DNAs were extracted from the strawberry varieties: "Miyazaki Natsu Haruka," "08 To-f," and "Ohkimi," the hybrid progeny lines of "Miyazaki Natsu Haruka" and "08 To-f" (Population A), and the hybrid progeny lines of "Miyazaki Natsu Haruka" and "Ohkimi" (Population B), using the Dneasy Plant Mini Kit (Qiagen).

(2) Preparation of Primer

With the use of PCR primer analytic software (Primer 3), primers that recognize the sequences of IB204594R were prepared on the basis of the sequence information thereof (SEQ ID NO: 4) (S40884_v1F: CCGGAGTACATGG-TAACCTATGC (SEQ ID NO: 9); S40884_v1R: TTTTCT-GCCTCGGTCATCTG (SEQ ID NO: 10)). IB204594R is a reciprocal marker that is not observed in everbearing lines.

(3) Amplification by PCR and Test of Selection Marker

The above pair of the primers (S40884_v1F and S40884_v1R) and Taq polymerase (1.25 units, Tks Gflex DNA Polymerase, Takara Bio Inc.) were added to the genomic DNAs (15 ng each) of the hybrid progeny lines: Population A and Population B, and the genomic DNAs were amplified by PCR (30 cycles of 94° C. for 1 minute, 98° C. for 10 seconds, 60° C. for 15 seconds, and 68° C. for 30 seconds, followed by storage at 4° C.). The PCR-amplified DNA fragment was confirmed using the TapeStation D1000 (Agilent). The results attained for Population A and Population B are shown in FIGS. 7-1 and 7-2 and FIGS. 8-1 and 8-2, respectively. In FIGS. 7-1 and 7-2 and 8-1 and 8-2, regions surrounded in frames represent phenotypes concerning everbearing properties. In FIGS. 7-1 to 8-2, lane M represents "Miyazaki Natsu Haruka" and lane Z represents "08 To-f" These results are summarized in FIGS. 9-1 and 9-2. In FIGS. 9-1 and 9-2, underlines are provided when phenotypes are not consistent with the results attained with the use of PCR base markers. As shown in FIGS. 7-1 to 9-2, the degree of consistency between band patterns and phenotypes is very high (i.e., 96.7%) and the method of nucleic acid amplification involving the use of primers that specifically amplify IB204594R enables selection of everbearing lines and one-season-bearing lines.

6. Selection and Test Using PCR Base Marker 2

(1) Extraction of Genomic DNA

Genomic DNAs were extracted from the strawberry varieties: "Miyazaki Natsu Haruka," "08 To-f," and "Ohkimi," the hybrid progeny lines of "Miyazaki Natsu Haruka" and "08 To-f" (Population A), and the hybrid progeny lines of "Miyazaki Natsu Haruka" and "Ohkimi" (Population B), using the Dneasy Plant Mini Kit (Qiagen).

(2) Preparation of Primer

With the use of PCR primer analytic software (Primer 3), primers that recognize the sequences of IBA38559 were prepared on the basis of the sequence information thereof (SEQ ID NO: 3) (S2430859_v1F: CGCCCATGTCTT-GAITCC (SEQ ID NO: 11) and S2430859_v1R: ATGAAT-TATTGCGCAGGCT (SEQ ID NO: 12)). IBA38559 is a coupling marker that is observed in everbearing lines.

(3) Amplification by PCR and Test of Selection Marker

The above pair of the primers (S2430859_v1F and S2430859_v1R) and Taq polymerase (1.25 units, Tks Gflex DNA Polymerase, Takara Bio Inc.) were added to the genomic DNAs (15 ng each) of the hybrid progeny lines: Population A and Population B, and the genomic DNAs were amplified by PCR (30 cycles of 94° C. for 1 minute, 98° C. for 10 seconds, 61° C. for 15 seconds, and 68° C. for 30 seconds, followed by storage at 4° C.). The PCR-amplified DNA fragment was confirmed using the TapeStation D1000 (Agilent). The results attained for Population A and Population B are shown in FIGS. 10-1 and 10-2 and FIGS. 11-1 and 11-2, respectively. In FIGS. 10-1 and 10-2 and FIGS. 11-1 and 11-2, regions surrounded in frames represent phenotypes concerning everbearing properties. In FIGS. 10-1 to 11-2, lane M represents "Miyazaki Natsu Haruka," and lane Z represents "08 To-f." These results are summarized in FIGS. 12-1 and 12-2. In FIGS. 12-1 and 12-2, underlines are provided when phenotypes are not consistent with the results attained with the use of PCR markers. As shown in FIGS. 10-1 to 12-2, the degree of consistency between band patterns and phenotypes is very high (i.e., 95.6%) and the method of nucleic acid amplification involving the use of primers that specifically amplify IBA38559 enables selection of everbearing lines and one-season-bearing lines.

All publications, patents, and patent applications cited herein are incorporated herein by reference in their entirety.

The invention claimed is:

1. A method for producing a plant line of the genus *Fragaria*, comprising:
   (a) extracting genomic DNA from a progeny plant whose at least one parent is a plant of the genus *Fragaria* or genomic DNA from a plant of the genus *Fragaria*;
   (b) determining by nucleic acid assay the quantity of a nucleic acid marker associated with everbearing properties in the genomic DNA of the plant, wherein the marker comprises the nucleotide sequence of SEQ ID NO: 3;
   (c) detecting a plant with an increased quantity of the marker compared to the quantity detected in one-season-bearing plants;
   (d) selecting the plant as a plant with everbearing properties; and
   (e) using the selected plant as a parent plant for crossing to thereby produce a plant line of the genus *Fragaria*.

2. The method for producing a plant line of the genus *Fragaria* according to claim 1, wherein the step of determination comprises conducting a nucleic acid amplification reaction using a primer that specifically amplifies the nucleic acid marker associated with everbearing properties in the genomic DNA of the plant to determine the quantity of the nucleic acid marker associated with everbearing properties in the genomic DNA of the plant.

3. The method for producing a plant line of the genus *Fragaria* according to claim 1, wherein the step of determination involves the use of a DNA chip comprising a probe corresponding to the nucleic acid marker associated with everbearing properties in the genomic DNA of the plant.

4. The method for producing a plant line of the genus *Fragaria* according to claim 1, wherein the progeny plant is a seed or seedling and the genomic DNA is extracted from the seed or seedling.

* * * * *

SEQUENCE LISTING

<160> NUMBER OF SEQ ID NOS: 12

<210> SEQ ID NO 1
<211> LENGTH: 744
<212> TYPE: DNA
<213> ORGANISM: Fragaria x ananassa

<400> SEQUENCE: 1

```
ttgatgtaga tatgatatat caaagagaag gaaaagaaac tttgccacac ttaagtctac      60
aagcatatct atacaaacac attcgttaaa tgtcaatagc atatcatcac aattcagttg     120
aaatagcatt ctaaacagat gctattgttc cttcagtaga tgcaccaagg acttctgtga     180
ctctgtgtcc agactccaaa ctatctcaaa ccagtaagat aatttccttt ttatacactt     240
cacacaagac aaaatgttta accatcactg atgctaagac cagattgaaa ggtcccgctg     300
ccaaaccatc ttgaccacat acaacaaaac atgaccttta gcaccataaa ttttccacaa     360
gtacaaattt acaagttaaa actgttcagt taaacacccc caccgtgact taatcactca     420
aagcaattga aagaaatcc aagttcccaa ctagtaaacg tattacaata ttcctctcac     480
agcttaaacg caaccgatt atgttgagtt gctaaccctt tacattgttg cattatgtgt     540
tctaagagca ttaatctaaa acaataaggg gtcattcaca ccattctaaa gcgcacaatc     600
agaagcttta ctttacttct cgagccaatt tcgcatatgt tacccaaatc ttcacatagt     660
tcaagcaaat ccaattttgc aaaacaccca acaaagcatg aatcgaatac ttaacattgc     720
aacaataaaa acaaagtttt caat                                            744
```

<210> SEQ ID NO 2
<211> LENGTH: 442
<212> TYPE: DNA
<213> ORGANISM: Fragaria x ananassa

<400> SEQUENCE: 2

```
aattctgtag aatcacccaa agatcttaac gagttacccc ttgaagatga agagttcaga      60
acgtgtgatg aaaagttttc tgatgaaaaa gtagcagagg aggggaagca aaatgaagag     120
gggacagaag tcgcagatgc tttctcaagg caagcagatg aagctagaaa cactgctgtc     180
taagtttgtg gacaggtaat tcctactcac gcacagttta attatttagt tcgtcatccc     240
ttctctcata aatactcata tactatgttc tctgaatttt caggtcgagt gctgatgaaa     300
cattgcttca catgaatgat gatcccttc tgaagaatag cttagttttt gtgtgatggc     360
ctgtgatttt ctattgtgaa actgtatcag tagtgtaaaa aattaaaaca taaaattgct     420
atcctaagaa gactaggata ga                                              442
```

<210> SEQ ID NO 3

```
<211> LENGTH: 311
<212> TYPE: DNA
<213> ORGANISM: Fragaria x ananassa

<400> SEQUENCE: 3
cacattgttc ttcactccgc ttccgaatag ctatatccat ttttctgagt gaacttggaa      60
ctaaagccta gcttgattaa ttccatctcg cccgcccatg tcttgattcc ctaaaactaa     120
acgaattgtt gtggattcca aatgatttgt ataatattat gaatcgccgt caaagtctac     180
ccgattcaga aactccaata atttacatga acaaacaaaa gcctgcgcaa taattcatgc     240
atgtttcatc tcaaactctc gaggattgat tctctctgtc ataagagc atatgcactc       300 catccctcc a                                                            311

<210> SEQ ID NO 4
<211> LENGTH: 507
<212> TYPE: DNA
<213> ORGANISM: Fragaria x ananassa

<400> SEQUENCE: 4
tgtgctttcc aagtttccat ttttgtttta gactgatgaa ttgtccaagt ccaagcaata      60
ataccgccaa atcaaccgg tcatgatact actaatatgg agcttgtact gtggtcgacg      120
acagaaagat cttatcgacc cgatgatgaa acatcatctg taacagttga agtgatataa    180
ctttgtagtt gctagaactt tgaaacgata ggtcgtaacg tatcaaaatt aaaacgttag    240
actaataaac cggagtacat ggtaacctat gctctcgttg ctatcattaa gcctctctcc    300
ccacataggc aatcatatac cctagagtct tagacttttt ttgggtacgc aaactgtctc    360
ttttgctgcg gggcagatga ccgaggcaga aaatatatt aacagagata caaaaatttc     420
ttgcggttaa attttagtaa caatatatat aagcacgact ataagcatta cttgcggcta    480
atttatgtgt acaagaattg aagtttg                                          507

<210> SEQ ID NO 5
<211> LENGTH: 475
<212> TYPE: DNA
<213> ORGANISM: Fragaria x ananassa

<400> SEQUENCE: 5
ttggaatgca gaactttgt tgctgtactt acgtaatttt gtgtatagtt gttcacttat       60
catttctagg catcaaagtt agaatctccc ttatccagaa ttggtatggt tctgtacagt     120
gtaatttagc tatctgtaat gagcttcatc cttgaagttt caattcggta agatcaaata    180
tccatccttg tcttggaaca aaaggctaag aaatgttaat catgtattga ctatggcact    240
actagtgatt gcatatgtta actcagaaat gtgatgttta cttaggttgg gaggtggcct    300
ataagcaact attctgattc ttcacaatca gtttagcagt tggagttta taagccagca    360 tatccaatac accaattgca agtctccaca cagctcaaaa tgagtgtagg aaactaaaaa    420
tacttcggac tccattctgt gcattaacag tgagaaactg agtaggcgag tagat           475

<210> SEQ ID NO 6
<211> LENGTH: 18
<212> TYPE: DNA
<213> ORGANISM: Artificial Sequence
<220> FEATURE:
<223> OTHER INFORMATION: Synthetic DNA

<400> SEQUENCE: 6
cacgatggat ccagtgca                                                     18
```

```
<210> SEQ ID NO 7
<211> LENGTH: 16
<212> TYPE: DNA
<213> ORGANISM: Artificial Sequence
<220> FEATURE:
<223> OTHER INFORMATION: Synthetic DNA

<400> SEQUENCE: 7
ctggatccat cgtgca                                                    16

<210> SEQ ID NO 8
<211> LENGTH: 16
<212> TYPE: DNA
<213> ORGANISM: Artificial Sequence
<220> FEATURE:
<223> OTHER INFORMATION: Synthetic DNA

<400> SEQUENCE: 8
gatggatcca gtgcag                                                    16

<210> SEQ ID NO 9
<211> LENGTH: 23
<212> TYPE: DNA
<213> ORGANISM: Artificial Sequence
<220> FEATURE:
<223> OTHER INFORMATION: Synthetic DNA

<400> SEQUENCE: 9
ccggagtaca tggtaaccta tgc                                            23

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
ttttctgcct cggtcatctg                                                20

<210> SEQ ID NO 11
<211> LENGTH: 18
<212> TYPE: DNA
<213> ORGANISM: Artificial Sequence
<220> FEATURE:
<223> OTHER INFORMATION: Synthetic DNA

<400> SEQUENCE: 11
cgcccatgtc ttgattcc                                                  18

<210> SEQ ID NO 12
<211> LENGTH: 19
<212> TYPE: DNA
<213> ORGANISM: Artificial Sequence
<220> FEATURE:
<223> OTHER INFORMATION: Synthetic DNA

<400> SEQUENCE: 12
atgaattatt gcgcaggct                                                 19
```